United States Patent
Taremi et al.

[11] Patent Number: 5,981,167
[45] Date of Patent: Nov. 9, 1999

[54] SURFACE PLASMON RESONANCE BASED ENZYMATIC ASSAY

[76] Inventors: Shahriar Shane Taremi, 12 Park Ter., Upper Montclair, N.J. 07043; Winifred W. Prosise, 16 E. Oak St., Ramsey, N.J. 07446

[21] Appl. No.: 09/021,480

[22] Filed: Feb. 10, 1998

Related U.S. Application Data

[63] Continuation of application No. 08/440,283, May 12, 1995.

[51] Int. Cl.[6] .................................................. C12Q 1/00
[52] U.S. Cl. ................... 435/4; 435/5; 435/7.4; 435/23; 435/24; 436/518
[58] Field of Search .................. 435/4, 7.4, 23, 435/24, 5; 436/518

[56] References Cited

U.S. PATENT DOCUMENTS

| | | | |
|---|---|---|---|
| 4,918,001 | 4/1990 | Kolde | 435/24 |
| 5,171,662 | 12/1992 | Sharma | 435/5 |
| 5,304,465 | 4/1994 | Garland et al. | 435/4 |
| 5,338,663 | 8/1994 | Potter et al. | 435/4 |
| 5,767,233 | 6/1998 | Zhang et al. | 530/326 |

FOREIGN PATENT DOCUMENTS

| | | |
|---|---|---|
| 0 245 926 | 3/1987 | European Pat. Off. . |
| WO 90/11510 | 10/1990 | WIPO . |
| WO 90/11525 | 10/1990 | WIPO . |
| WO 90/15983 | 12/1990 | WIPO . |
| WO 92/18867 | 10/1992 | WIPO . |

OTHER PUBLICATIONS

Tachikawa et al., 1991, *Clinical Chemistry* 37(12):2081–86.
Choquette et al., 1992, *Analytical Chemistry* 64:55–60.
Holskin et al. "A Continuous Fluorescence–Based Assay of Human Cytomegalovirus Protease Using a Peptide Substrate", *Analytical Biochemistry*, vol. 227, No. 1(May 1, 1995), pp. 148–155.

*Primary Examiner*—Jeffrey Stucker
*Attorney, Agent, or Firm*—J. P. McLaughlin

[57] ABSTRACT

A method for determining if an enzyme can cleave a substrate or if a substance is an inhibitor of the enzyme using surface plamon resonance.

14 Claims, 9 Drawing Sheets

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 549 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: HCV NS3 Protease (xi) SEQUENCE DESCRIPTION: SEQ ID NO: 1:

| | | | | | | | | | | | | | | |
|---|---|---|---|---|---|---|---|---|---|---|---|---|---|---|
| GCG | CCC | ATC | ACG | GCG | TAC | GCC | CAG | CAG | ACG | AGA | GGC | CTC | CTA | GGG | 45
| Ala | Pro | Ile | Thr | Ala | Tyr | Ala | Gln | Gln | Thr | Arg | Gly | Leu | Leu | Gly |
| 1 | | | | 5 | | | | | 10 | | | | | 15 |

| | | | | | | | | | | | | | | |
|---|---|---|---|---|---|---|---|---|---|---|---|---|---|---|
| TGT | ATA | ATC | ACC | AGC | CTG | ACT | GGC | CGG | GAC | AAA | AAC | CAA | GTG | GAG | 90
| Cys | Ile | Ile | Thr | Ser | Leu | Thr | Gly | Arg | Asp | Lys | Asn | Gln | Val | Glu |
| | | | | 20 | | | | | 25 | | | | | 30 |

| | | | | | | | | | | | | | | |
|---|---|---|---|---|---|---|---|---|---|---|---|---|---|---|
| GGT | GAG | GTC | CAG | ATC | GTG | TCA | ACT | GCT | ACC | CAA | ACC | TTC | CTG | GCA | 135
| Gly | Glu | Val | Gln | Ile | Val | Ser | Thr | Ala | Thr | Gln | Thr | Phe | Leu | Ala |
| | | | | 35 | | | | | 40 | | | | | 45 |

| | | | | | | | | | | | | | | |
|---|---|---|---|---|---|---|---|---|---|---|---|---|---|---|
| ACG | TGC | ATC | AAT | GGG | GTA | TGC | TGG | ACT | GTC | TAC | CAC | GGG | GCC | GGA | 180
| Thr | Cys | Ile | Asn | Gly | Val | Cys | Trp | Thr | Val | Tyr | His | Gly | Ala | Gly |
| | | | | 50 | | | | | 55 | | | | | 60 |

| | | | | | | | | | | | | | | |
|---|---|---|---|---|---|---|---|---|---|---|---|---|---|---|
| ACG | AGG | ACC | ATC | GCA | TCA | CCC | AAG | GGT | CCT | GTC | ATC | CAG | ATG | TAT | 225
| Thr | Arg | Thr | Ile | Ala | Ser | Pro | Lys | Gly | Pro | Val | Ile | Gln | Met | Tyr |
| | | | | 65 | | | | | 70 | | | | | 75 |

| | | | | | | | | | | | | | | |
|---|---|---|---|---|---|---|---|---|---|---|---|---|---|---|
| ACC | AAT | GTG | GAC | CAA | GAC | CTT | GTG | GGC | TGG | CCC | GCT | CCT | CAA | GGT | 270
| Thr | Asn | Val | Asp | Gln | Asp | Leu | Val | Gly | Trp | Pro | Ala | Pro | Gln | Gly |
| | | | | 80 | | | | | 85 | | | | | 90 |

| | | | | | | | | | | | | | | |
|---|---|---|---|---|---|---|---|---|---|---|---|---|---|---|
| TCC | CGC | TCA | TTG | ACA | CCC | TGC | ACC | TGC | GGC | TCC | TCG | GAC | CTT | TAC | 315
| Ser | Arg | Ser | Leu | Thr | Pro | Cys | Thr | Cys | Gly | Ser | Ser | Asp | Leu | Tyr |
| | | | | 95 | | | | | 100 | | | | | 105 |

| | | | | | | | | | | | | | | |
|---|---|---|---|---|---|---|---|---|---|---|---|---|---|---|
| CTG | GTT | ACG | AGG | CAC | GCC | GAC | GTC | ATT | CCC | GTG | CGC | CGG | CGA | GGT | 360
| Leu | Val | Thr | Arg | His | Ala | Asp | Val | Ile | Pro | Val | Arg | Arg | Arg | Gly |
| | | | | 110 | | | | | 115 | | | | | 120 |

| | | | | | | | | | | | | | | |
|---|---|---|---|---|---|---|---|---|---|---|---|---|---|---|
| GAT | AGC | AGG | GGT | AGC | CTG | CTT | TCG | CCC | CGG | CCC | ATT | TCC | TAC | CTA | 405
| Asp | Ser | Arg | Gly | Ser | Leu | Leu | Ser | Pro | Arg | Pro | Ile | Ser | Tyr | Leu |
| | | | | 125 | | | | | 130 | | | | | 135 |

| | | | | | | | | | | | | | | |
|---|---|---|---|---|---|---|---|---|---|---|---|---|---|---|
| AAA | GGC | TCC | TCG | GGG | GGT | CCG | CTG | TTG | TGC | CCC | GCG | GGA | CAC | GCC | 450
| Lys | Gly | Ser | Ser | Gly | Gly | Pro | Leu | Leu | Cys | Pro | Ala | Gly | His | Ala |
| | | | | 140 | | | | | 145 | | | | | 150 |

| | | | | | | | | | | | | | | |
|---|---|---|---|---|---|---|---|---|---|---|---|---|---|---|
| GTG | GGC | CTA | TTC | AGG | GCC | GCG | GTG | TGC | ACC | CGT | GGA | GTG | ACC | AAG | 495
| Val | Gly | Leu | Phe | Arg | Ala | Ala | Val | Cys | Thr | Arg | Gly | Val | Thr | Lys |
| | | | | 155 | | | | | 160 | | | | | 165 |

| | | | | | | | | | | | | | | |
|---|---|---|---|---|---|---|---|---|---|---|---|---|---|---|
| GCG | GTG | GAC | TTT | ATC | CCT | GTG | GAG | AAC | CTA | GAG | ACA | ACC | ATG | AGA | 540
| Ala | Val | Asp | Phe | Ile | Pro | Val | Glu | Asn | Leu | Glu | Thr | Thr | Met | Arg |
| | | | | 170 | | | | | 175 | | | | | 180 |

| | | |
|---|---|---|
| TCC | CCG | GTG | 549
| Ser | Pro | Val |

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Arg Lys Lys Lys Arg Arg
               5

(2) INFORMATION FOR SEQ ID NO:3:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: cDNA

19

-continued (xi) SEQUENCE DESCRIPTION: SEQ ID NO: 3:

```
GCG CCC ATC ACG GCG TAC GCC CAG CAG ACG AGA GGC CTC CTA GGG        45
Ala Pro Ile Thr Ala Tyr Ala Gln Gln Thr Arg Gly Leu Leu Gly
 1               5                  10                  15

TGT ATA ATC ACC AGC CTG ACT GGC CGG GAC AAA AAC CAA GTG GAG        90
Cys Ile Ile Thr Ser Leu Thr Gly Arg Asp Lys Asn Gln Val Glu
                20                  25                  30

GGT GAG GTC CAG ATC GTG TCA ACT GCT ACC CAA ACC TTC CTG GCA       135
Gly Glu Val Gln Ile Val Ser Thr Ala Thr Gln Thr Phe Leu Ala
            35                  40                  45

ACG TGC ATC AAT GGG GTA TGC TGG ACT GTC TAC CAC GGG GCC GGA       180
Thr Cys Ile Asn Gly Val Cys Trp Thr Val Tyr His Gly Ala Gly
        50                  55                  60

ACG AGG ACC ATC GCA TCA CCC AAG GGT CCT GTC ATC CAG ATG TAT       225
Thr Arg Thr Ile Ala Ser Pro Lys Gly Pro Val Ile Gln Met Tyr
    65                  70                  75

ACC AAT GTG GAC CAA GAC CTT GTG GGC TGG CCC GCT CCT CAA GGT       270
Thr Asn Val Asp Gln Asp Leu Val Gly Trp Pro Ala Pro Gln Gly
80                  85                  90

TCC CGC TCA TTG ACA CCC TGC ACC TGC GGC TCC TCG GAC CTT TAC       315
Ser Arg Ser Leu Thr Pro Cys Thr Cys Gly Ser Ser Asp Leu Tyr
                95                  100                 105

CTG GTT ACG AGG CAC GCC GAC GTC ATT CCC GTG CGC CGG CGA GGT       360
Leu Val Thr Arg His Ala Asp Val Ile Pro Val Arg Arg Arg Gly
            110                 115                 120

GAT AGC AGG GGT AGC CTG CTT TCG CCC CGG CCC ATT TCC TAC CTA       405
Asp Ser Arg Gly Ser Leu Leu Ser Pro Arg Pro Ile Ser Tyr Leu
        125                 130                 135

AAA GGC TCC TCG GGG GGT CCG CTG TTG TGC CCC GCG GGA CAC GCC       450
Lys Gly Ser Ser Gly Gly Pro Leu Leu Cys Pro Ala Gly His Ala
    140                 145                 150

GTG GGC CTA TTC AGG GCC GCG GTG TGC ACC CGT GGA GTG ACC AAG       495
Val Gly Leu Phe Arg Ala Ala Val Cys Thr Arg Gly Val Thr Lys
155                 160                 165

GCG GTG GAC TTT ATC CCT GTG GAG AAC CTA GAG ACA ACC ATG AGA       540
Ala Val Asp Phe Ile Pro Val Glu Asn Leu Glu Thr Thr Met Arg
                170                 175                 180

TCC CCG GTG AGA AAG AAG AAG AGA AGA                               567
Ser Pro Val Arg Lys Lys Lys Arg Arg
                185
```

(2) INFORMATION FOR SEQ ID NO:4:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: pBJ1022(His/NS3 (182)/H.T.

(xi) SEQUENCE DESCRIPTION: SEQ ID NO: 4:

```
ATG AGA GGA TCG CAT CAC CAT CAC CAT CAC ACG GAT CCG CCC ATC        45
Met Arg Gly Ser His His His His His His Thr Asp Pro Pro Ile
 1               5                  10                  15

ACG GCG TAC GCC CAG CAG ACG AGA GGC CTC CTA GGG TGT ATA ATC        90
Thr Ala Tyr Ala Gln Gln Thr Arg Gly Leu Leu Gly Cys Ile Ile
                20                  25                  30

ACC AGC CTG ACT GGC CGG GAC AAA AAC CAA GTG GAG GGT GAG GTC       135
Thr Ser Leu Thr Gly Arg Asp Lys Asn Gln Val Glu Gly Glu Val
```

```
                        35                  40                  45
CAG ATC GTG TCA ACT GCT ACC CAA ACC TTC CTG GCA ACG TGC ATC              180
Gln Ile Val Ser Thr Ala Thr Gln Thr Phe Leu Ala Thr Cys Ile
                50                  55                  60

AAT GGG GTA TGC TGG ACT GTC TAC CAC GGG GCC GGA ACG AGG ACC              225
Asn Gly Val Cys Trp Thr Val Tyr His Gly Ala Gly Thr Arg Thr
                65                  70                  75

ATC GCA TCA CCC AAG GGT CCT GTC ATC CAG ATG TAT ACC AAT GTG              270
Ile Ala Ser Pro Lys Gly Pro Val Ile Gln Met Tyr Thr Asn Val
                80                  85                  90

GAC CAA GAC CTT GTG GGC TGG CCC GCT CCT CAA GGT TCC CGC TCA              315
Asp Gln Asp Leu Val Gly Trp Pro Ala Pro Gln Gly Ser Arg Ser
                95                 100                 105

TTG ACA CCC TGC ACC TGC GGC TCC TCG GAC CTT TAC CTG GTT ACG              360
Leu Thr Pro Cys Thr Cys Gly Ser Ser Asp Leu Tyr Leu Val Thr
               110                 115                 120

AGG CAC GCC GAC GTC ATT CCC GTG CGC CGG CGA GGT GAT AGC AGG              405
Arg His Ala Asp Val Ile Pro Val Arg Arg Arg Gly Asp Ser Arg
               125                 130                 135

GGT AGC CTG CTT TCG CCC CGG CCC ATT TCC TAC CTA AAA GGC TCC              450
Gly Ser Leu Leu Ser Pro Arg Pro Ile Ser Tyr Leu Lys Gly Ser
               140                 145                 150

TCG GGG GGT CCG CTG TTG TGC CCC GCG GGA CAC GCC GTG GGC CTA              495
Ser Gly Gly Pro Leu Leu Cys Pro Ala Gly His Ala Val Gly Leu
               155                 160                 165

TTC AGG GCC GCG GTG TGC ACC CGT GGA GTG ACC AAG GCG GTG GAC              540
Phe Arg Ala Ala Val Cys Thr Arg Gly Val Thr Lys Ala Val Asp
               170                 175                 180

TTT ATC CCT GTG GAG AAC CTA GAG ACA ACC ATG AGA TCC CCG GTG              585
Phe Ile Pro Val Glu Asn Leu Glu Thr Thr Met Arg Ser Pro Val
               185                 190                 195

AGA AAG AAG AAG AGA AGA                                                  603
Arg Lys Lys Lys Arg Arg
               200

(2) INFORMATION FOR SEQ ID NO:5:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: pT5His/HIV/183 No solubilizing motif (xi) SEQUENCE DESCRIPTION: SEQ ID NO: 5:

ATG AGA GGA TCG CAT CAC CAT CAC CAT CAC GGA TCC CAT AAG GCA               45
Met Arg Gly Ser His His His His His His Gly Ser His Lys Ala
1               5                  10                  15

AGA GTT TTG GCT GAA GCA ATG AGC CAT GGT ACC ATG GCG CCC ATC               90
Arg Val Leu Ala Glu Ala Met Ser His Gly Thr Met Ala Pro Ile
                20                  25                  30

ACG GCG TAC GCC CAG CAG ACG AGA GGC CTC CTA GGG TGT ATA ATC              135
Thr Ala Tyr Ala Gln Gln Thr Arg Gly Leu Leu Gly Cys Ile Ile
                35                  40                  45

ACC AGC CTG ACT GGC CGG GAC AAA AAC CAA GTG GAG GGT GAG GTC              180
Thr Ser Leu Thr Gly Arg Asp Lys Asn Gln Val Glu Gly Glu Val
                50                  55                  60

CAG ATC GTG TCA ACT GCT ACC CAA ACC TTC CTG GCA ACG TGC ATC              225
Gln Ile Val Ser Thr Ala Thr Gln Thr Phe Leu Ala Thr Cys Ile
```

```
                        65                  70                  75
AAT GGG GTA TGC TGG ACT GTC TAC CAC GGG GCC GGA ACG AGG ACC           270
Asn Gly Val Cys Trp Thr Val Tyr His Gly Ala Gly Thr Arg Thr
                80                  85                  90

ATC GCA TCA CCC AAG GGT CCT GTC ATC CAG ATG TAT ACC AAT GTG           315
Ile Ala Ser Pro Lys Gly Pro Val Ile Gln Met Tyr Thr Asn Val
                95                  100                 105

GAC CAA GAC CTT GTG GGC TGG CCC GCT CCT CAA GGT TCC CGC TCA           360
Asp Gln Asp Leu Val Gly Trp Pro Ala Pro Gln Gly Ser Arg Ser
                110                 115                 120

TTG ACA CCC TGC ACC TGC GGC TCC TCG GAC CTT TAC CTG GTT ACG           405
Leu Thr Pro Cys Thr Cys Gly Ser Ser Asp Leu Tyr Leu Val Thr
                125                 130                 135

AGG CAC GCC GAC GTC ATT CCC GTG CGC CGG CGA GGT GAT AGC AGG           450
Arg His Ala Asp Val Ile Pro Val Arg Arg Arg Gly Asp Ser Arg
                140                 145                 150

GGT AGC CTG CTT TCG CCC CGG CCC ATT TCC TAC CTA AAA GGC TCC           495
Gly Ser Leu Leu Ser Pro Arg Pro Ile Ser Tyr Leu Lys Gly Ser
                155                 160                 165

TCG GGG GGT CCG CTG TTG TGC CCC GCG GGA CAC GCC GTG GGC CTA           540
Ser Gly Gly Pro Leu Leu Cys Pro Ala Gly His Ala Val Gly Leu
                170                 175                 180

TTC AGG GCC GCG GTG TGC ACC CGT GGA GTG ACC AAG GCG GTG GAC           585
Phe Arg Ala Ala Val Cys Thr Arg Gly Val Thr Lys Ala Val Asp
                185                 190                 195

TTT ATC CCT GTG GAG AAC CTA GAG ACA ACC ATG AGA TCC CCG GTG           630
Phe Ile Pro Val Glu Asn Leu Glu Thr Thr Met Arg Ser Pro Val
                200                 205                 210

(2) INFORMATION FOR SEQ ID NO:6:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: NS4A (xi) SEQUENCE DESCRIPTION: SEQ ID NO: 6:

AGC ACC TGG GTG CTC GTT GGC GGC GTC CTG GCT GCT CTG GCC GCG            45
Ser Thr Trp Val Leu Val Gly Gly Val Leu Ala Ala Leu Ala Ala
1               5                   10                  15

TAT TGC CTG TCA ACA GGC TGC GTG GTC ATA GTG GGC AGG ATT GTC            90
Tyr Cys Leu Ser Thr Gly Cys Val Val Ile Val Gly Arg Ile Val
                20                  25                  30

TTG TCC GGG AAG CCG GCA ATT ATA CCT GAC AGG GAG GTT CTC TAC           135
Leu Ser Gly Lys Pro Ala Ile Ile Pro Asp Arg Glu Val Leu Tyr
                35                  40                  45

CAG GAG TTC GAT GAG ATG GAA GAG TGC                                   162
Gln Glu Phe Asp Glu Met Glu Glu Cys
                50

(2) INFORMATION FOR SEQ ID NO:7:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: cDNA
```

```
        (ix) FEATURE:
              (A) NAME/KEY: NS3 +NS4A (xi) SEQUENCE DESCRIPTION: SEQ ID NO: 7:

GCG CCC ATC ACG GCG TAC GCC CAG CAG ACG AGA GGC CTC CTA GGG         45
Ala Pro Ile Thr Ala Tyr Ala Gln Gln Thr Arg Gly Leu Leu Gly
 1               5                  10                  15

TGT ATA ATC ACC AGC CTG ACT GGC CGG GAC AAA AAC CAA GTG GAG         90
Cys Ile Ile Thr Ser Leu Thr Gly Arg Asp Lys Asn Gln Val Glu
                20                  25                  30

GGT GAG GTC CAG ATC GTG TCA ACT GCT ACC CAA ACC TTC CTG GCA        135
Gly Glu Val Gln Ile Val Ser Thr Ala Thr Gln Thr Phe Leu Ala
             35                  40                  45

ACG TGC ATC AAT GGG GTA TGC TGG ACT GTC TAC CAC GGG GCC GGA        180
Thr Cys Ile Asn Gly Val Cys Trp Thr Val Tyr His Gly Ala Gly
             50                  55                  60

ACG AGG ACC ATC GCA TCA CCC AAG GGT CCT GTC ATC CAG ATG TAT        225
Thr Arg Thr Ile Ala Ser Pro Lys Gly Pro Val Ile Gln Met Tyr
             65                  70                  75

ACC AAT GTG GAC CAA GAC CTT GTG GGC TGG CCC GCT CCT CAA GGT        270
Thr Asn Val Asp Gln Asp Leu Val Gly Trp Pro Ala Pro Gln Gly
             80                  85                  90

TCC CGC TCA TTG ACA CCC TGC ACC TGC GGC TCC TCG GAC CTT TAC        315
Ser Arg Ser Leu Thr Pro Cys Thr Cys Gly Ser Ser Asp Leu Tyr
             95                 100                 105

CTG GTT ACG AGG CAC GCC GAC GTC ATT CCC GTG CGC CGG CGA GGT        360
Leu Val Thr Arg His Ala Asp Val Ile Pro Val Arg Arg Arg Gly
            110                 115                 120

GAT AGC AGG GGT AGC CTG CTT TCG CCC CGG CCC ATT TCC TAC CTA        405
Asp Ser Arg Gly Ser Leu Leu Ser Pro Arg Pro Ile Ser Tyr Leu
            125                 130                 135

AAA GGC TCC TCG GGG GGT CCG CTG TTG TGC CCC GCG GGA CAC GCC        450
Lys Gly Ser Ser Gly Gly Pro Leu Leu Cys Pro Ala Gly His Ala
            140                 145                 150

GTG GGC CTA TTC AGG GCC GCG GTG TGC ACC CGT GGA GTG ACC AAG        495
Val Gly Leu Phe Arg Ala Ala Val Cys Thr Arg Gly Val Thr Lys
            155                 160                 165

GCG GTG GAC TTT ATC CCT GTG GAG AAC CTA GAG ACA ACC ATG AGA        540
Ala Val Asp Phe Ile Pro Val Glu Asn Leu Glu Thr Thr Met Arg
            170                 175                 180

TCC CCG GGG GTG CTC GTT GGC GGC GTC CTG GCT GCT CTG GCC GCG        585
Ser Pro Gly Val Leu Val Gly Gly Val Leu Ala Ala Leu Ala Ala
            185                 190                 195

TAT TGC CTG TCA ACA GGC TGC GTG GTC ATA GTG GGC AGG ATT GTC        630
Tyr Cys Leu Ser Thr Gly Cys Val Val Ile Val Gly Arg Ile Val
            200                 205                 210

TTG TCC GGG AAG CCG GCA ATT ATA CCT GAC AGG GAG GTT CTC TAC        675
Leu Ser Gly Lys Pro Ala Ile Ile Pro Asp Arg Glu Val Leu Tyr
            215                 220                 225

CAG GAG TTC GAT GAG ATG GAA GAG TGC                                702
Gln Glu Phe Asp Glu Met Glu Glu Cys
            230
```

(2) INFORMATION FOR SEQ ID NO:8:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: pNB182_4AHT (xi) SEQUENCE DESCRIPTION: SEQ ID NO: 8:

| | | | | | | | | | | | | | | |
|---|---|---|---|---|---|---|---|---|---|---|---|---|---|---|
| ATG | AGA | GGA | TCG | CAT | CAC | CAT | CAC | CAT | CAC | GGA | TCC | CAT | AAG | GCA | 45 |
| Met | Arg | Gly | Ser | His | His | His | His | His | His | Gly | Ser | His | Lys | Ala |
| 1 | | | | 5 | | | | | 10 | | | | | 15 |

| AGA | GTT | TTG | GCT | GAA | GCA | ATG | AGC | CAT | GGT | ACC | ATG | GCG | CCC | ATC | 90 |
| Arg | Val | Leu | Ala | Glu | Ala | Met | Ser | His | Gly | Thr | Met | Ala | Pro | Ile |
| | | | | 20 | | | | | 25 | | | | | 30 |

| ACG | GCG | TAC | GCC | CAG | CAG | ACG | AGA | GGC | CTC | CTA | GGG | TGT | ATA | ATC | 135 |
| Thr | Ala | Tyr | Ala | Gln | Gln | Thr | Arg | Gly | Leu | Leu | Gly | Cys | Ile | Ile |
| | | | | 35 | | | | | 40 | | | | | 45 |

| ACC | AGC | CTG | ACT | GGC | CGG | GAC | AAA | AAC | CAA | GTG | GAG | GGT | GAG | GTC | 180 |
| Thr | Ser | Leu | Thr | Gly | Arg | Asp | Lys | Asn | Gln | Val | Glu | Gly | Glu | Val |
| | | | | 50 | | | | | 55 | | | | | 60 |

| CAG | ATC | GTG | TCA | ACT | GCT | ACC | CAA | ACC | TTC | CTG | GCA | ACG | TGC | ATC | 225 |
| Gln | Ile | Val | Ser | Thr | Ala | Thr | Gln | Thr | Phe | Leu | Ala | Thr | Cys | Ile |
| | | | | 65 | | | | | 70 | | | | | 75 |

| AAT | GGG | GTA | TGC | TGG | ACT | GTC | TAC | CAC | GGG | GCC | GGA | ACG | AGG | ACC | 270 |
| Asn | Gly | Val | Cys | Trp | Thr | Val | Tyr | His | Gly | Ala | Gly | Thr | Arg | Thr |
| | | | | 80 | | | | | 85 | | | | | 90 |

| ATC | GCA | TCA | CCC | AAG | GGT | CCT | GTC | ATC | CAG | ATG | TAT | ACC | AAT | GTG | 315 |
| Ile | Ala | Ser | Pro | Lys | Gly | Pro | Val | Ile | Gln | Met | Tyr | Thr | Asn | Val |
| | | | | 95 | | | | | 100 | | | | | 105 |

| GAC | CAA | GAC | CTT | GTG | GGC | TGG | CCC | GCT | CCT | CAA | GGT | TCC | CGC | TCA | 360 |
| Asp | Gln | Asp | Leu | Val | Gly | Trp | Pro | Ala | Pro | Gln | Gly | Ser | Arg | Ser |
| | | | | 110 | | | | | 115 | | | | | 120 |

| TTG | ACA | CCC | TGC | ACC | TGC | GGC | TCC | TCG | GAC | CTT | TAC | CTG | GTT | ACG | 405 |
| Leu | Thr | Pro | Cys | Thr | Cys | Gly | Ser | Ser | Asp | Leu | Tyr | Leu | Val | Thr |
| | | | | 125 | | | | | 130 | | | | | 135 |

| AGG | CAC | GCC | GAC | GTC | ATT | CCC | GTG | CGC | CGG | CGA | GGT | GAT | AGC | AGG | 450 |
| Arg | His | Ala | Asp | Val | Ile | Pro | Val | Arg | Arg | Arg | Gly | Asp | Ser | Arg |
| | | | | 140 | | | | | 145 | | | | | 150 |

| GGT | AGC | CTG | CTT | TCG | CCC | CGG | CCC | ATT | TCC | TAC | CTA | AAA | GGC | TCC | 495 |
| Gly | Ser | Leu | Leu | Ser | Pro | Arg | Pro | Ile | Ser | Tyr | Leu | Lys | Gly | Ser |
| | | | | 155 | | | | | 160 | | | | | 165 |

| TCG | GGG | GGT | CCG | CTG | TTG | TGC | CCC | GCG | GGA | CAC | GCC | GTG | GGC | CTA | 540 |
| Ser | Gly | Gly | Pro | Leu | Leu | Cys | Pro | Ala | Gly | His | Ala | Val | Gly | Leu |
| | | | | 170 | | | | | 175 | | | | | 180 |

| TTC | AGG | GCC | GCG | GTG | TGC | ACC | CGT | GGA | GTG | ACC | AAG | GCG | GTG | GAC | 585 |
| Phe | Arg | Ala | Ala | Val | Cys | Thr | Arg | Gly | Val | Thr | Lys | Ala | Val | Asp |
| | | | | 185 | | | | | 190 | | | | | 195 |

| TTT | ATC | CCT | GTG | GAG | AAC | CTA | GAG | ACA | ACC | ATG | AGA | TCC | CCG | GGG | 630 |
| Phe | Ile | Pro | Val | Glu | Asn | Leu | Glu | Thr | Thr | Met | Arg | Ser | Pro | Gly |
| | | | | 200 | | | | | 205 | | | | | 210 |

| GTG | CTC | GTT | GGC | GGC | GTC | CTG | GCT | GCT | CTG | GCC | GCG | TAT | TGC | CTG | 675 |
| Val | Leu | Val | Gly | Gly | Val | Leu | Ala | Ala | Leu | Ala | Ala | Tyr | Cys | Leu |
| | | | | 215 | | | | | 220 | | | | | 225 |

| TCA | ACA | GGC | TGC | GTG | GTC | ATA | GTG | GGC | AGG | ATT | GTC | TTG | TCC | GGG | 720 |
| Ser | Thr | Gly | Cys | Val | Val | Ile | Val | Gly | Arg | Ile | Val | Leu | Ser | Gly |
| | | | | 230 | | | | | 235 | | | | | 240 |

| AAG | CCG | GCA | ATT | ATA | CCT | GAC | AGG | GAG | GTT | CTC | TAC | CAG | GAG | TTC | 765 |
| Lys | Pro | Ala | Ile | Ile | Pro | Asp | Arg | Glu | Val | Leu | Tyr | Gln | Glu | Phe |
| | | | | 245 | | | | | 250 | | | | | 255 |

| GAT | GAG | ATG | GAA | GAG | TGC | CGG | AAG | AAA | AAG | AGA | CGC | AAG | CTT | AAT | 810 |
| Asp | Glu | Met | Glu | Glu | Cys | Arg | Lys | Lys | Lys | Arg | Arg | Lys | Leu | Asn |
| | | | | 260 | | | | | 265 | | | | | 270 |

(2) INFORMATION FOR SEQ ID NO:9:

(i) SEQUENCE CHARACTERISTICS:
    (A) LENGTH: 711 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 9:

```
GCG CCC ATC ACG GCG TAC GCC CAG CAG ACG AGA GGC CTC CTA GGG          45
Ala Pro Ile Thr Ala Tyr Ala Gln Gln Thr Arg Gly Leu Leu Gly
 1               5                  10                  15

TGT ATA ATC ACC AGC CTG ACT GGC CGG GAC AAA AAC CAA GTG GAG          90
Cys Ile Ile Thr Ser Leu Thr Gly Arg Asp Lys Asn Gln Val Glu
                20                  25                  30

GGT GAG GTC CAG ATC GTG TCA ACT GCT ACC CAA ACC TTC CTG GCA         135
Gly Glu Val Gln Ile Val Ser Thr Ala Thr Gln Thr Phe Leu Ala
            35                  40                  45

ACG TGC ATC AAT GGG GTA TGC TGG ACT GTC TAC CAC GGG GCC GGA         180
Thr Cys Ile Asn Gly Val Cys Trp Thr Val Tyr His Gly Ala Gly
        50                  55                  60

ACG AGG ACC ATC GCA TCA CCC AAG GGT CCT GTC ATC CAG ATG TAT         225
Thr Arg Thr Ile Ala Ser Pro Lys Gly Pro Val Ile Gln Met Tyr
    65                  70                  75

ACC AAT GTG GAC CAA GAC CTT GTG GGC TGG CCC GCT CCT CAA GGT         270
Thr Asn Val Asp Gln Asp Leu Val Gly Trp Pro Ala Pro Gln Gly
                80                  85                  90

TCC CGC TCA TTG ACA CCC TGC ACC TGC GGC TCC TCG GAC CTT TAC         315
Ser Arg Ser Leu Thr Pro Cys Thr Cys Gly Ser Ser Asp Leu Tyr
                95                 100                 105

CTG GTT ACG AGG CAC GCC GAC GTC ATT CCC GTG CGC CGG CGA GGT         360
Leu Val Thr Arg His Ala Asp Val Ile Pro Val Arg Arg Arg Gly
            110                 115                 120

GAT AGC AGG GGT AGC CTG CTT TCG CCC CGG CCC ATT TCC TAC CTA         405
Asp Ser Arg Gly Ser Leu Leu Ser Pro Arg Pro Ile Ser Tyr Leu
        125                 130                 135

AAA GGC TCC TCG GGG GGT CCG CTG TTG TGC CCC GCG GGA CAC GCC         450
Lys Gly Ser Ser Gly Gly Pro Leu Leu Cys Pro Ala Gly His Ala
    140                 145                 150

GTG GGC CTA TTC AGG GCC GCG GTG TGC ACC CGT GGA GTG ACC AAG         495
Val Gly Leu Phe Arg Ala Ala Val Cys Thr Arg Gly Val Thr Lys
155                 160                 165

GCG GTG GAC TTT ATC CCT GTG GAG AAC CTA GAG ACA ACC ATG AGA         540
Ala Val Asp Phe Ile Pro Val Glu Asn Leu Glu Thr Thr Met Arg
                170                 175                 180

TCC CCG GGG GTG CTC GTT GGC GGC GTC CTG GCT GCT CTG GCC GCG         585
Ser Pro Gly Val Leu Val Gly Gly Val Leu Ala Ala Leu Ala Ala
            185                 190                 195

TAT TGC CTG TCA ACA GGC TGC GTG GTC ATA GTG GGC AGG ATT GTC         630
Tyr Cys Leu Ser Thr Gly Cys Val Val Ile Val Gly Arg Ile Val
        200                 205                 210

TTG TCC GGG AAG CCG GCA ATT ATA CCT GAC AGG GAG GTT CTC TAC         675
Leu Ser Gly Lys Pro Ala Ile Ile Pro Asp Arg Glu Val Leu Tyr
    215                 220                 225

CAG GAG TTC GAT GAG ATG GAA GAG AAG GAG ACA GAG                    711
Gln Glu Phe Asp Glu Met Glu Glu Lys Glu Thr Glu
                230                 235
```

(2) INFORMATION FOR SEQ ID NO:10:

(i) SEQUENCE CHARACTERISTICS:
        (A) LENGTH: 750 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 10:

| | | | | | | | | | | | | | | | |
|---|---|---|---|---|---|---|---|---|---|---|---|---|---|---|---|
| ATG | AGA | GGA | TCG | CAT | CAC | CAT | CAC | CAT | CAC | ACG | GAT | CCG | GCG | CCC | 45 |
| Met | Arg | Gly | Ser | His | His | His | His | His | His | Thr | Asp | Pro | Ala | Pro | |
| 1 | | | | 5 | | | | | 10 | | | | | 15 | |
| ATC | ACG | GCG | TAC | GCC | CAG | CAG | ACG | AGA | GGC | CTC | CTA | GGG | TGT | ATA | 90 |
| Ile | Thr | Ala | Tyr | Ala | Gln | Gln | Thr | Arg | Gly | Leu | Leu | Gly | Cys | Ile | |
| | | | | 20 | | | | | 25 | | | | | 30 | |
| ATC | ACC | AGC | CTG | ACT | GGC | CGG | GAC | AAA | AAC | CAA | GTG | GAG | GGT | GAG | 135 |
| Ile | Thr | Ser | Leu | Thr | Gly | Arg | Asp | Lys | Asn | Gln | Val | Glu | Gly | Glu | |
| | | | | 35 | | | | | 40 | | | | | 45 | |
| GTC | CAG | ATC | GTG | TCA | ACT | GCT | ACC | CAA | ACC | TTC | CTG | GCA | ACG | TGC | 180 |
| Val | Gln | Ile | Val | Ser | Thr | Ala | Thr | Gln | Thr | Phe | Leu | Ala | Thr | Cys | |
| | | | | 50 | | | | | 55 | | | | | 60 | |
| ATC | AAT | GGG | GTA | TGC | TGG | ACT | GTC | TAC | CAC | GGG | GCC | GGA | ACG | AGG | 225 |
| Ile | Asn | Gly | Val | Cys | Trp | Thr | Val | Tyr | His | Gly | Ala | Gly | Thr | Arg | |
| | | | | 65 | | | | | 70 | | | | | 75 | |
| ACC | ATC | GCA | TCA | CCC | AAG | GGT | CCT | GTC | ATC | CAG | ATG | TAT | ACC | AAT | 270 |
| Thr | Ile | Ala | Ser | Pro | Lys | Gly | Pro | Val | Ile | Gln | Met | Tyr | Thr | Asn | |
| | | | | 80 | | | | | 85 | | | | | 90 | |
| GTG | GAC | CAA | GAC | CTT | GTG | GGC | TGG | CCC | GCT | CCT | CAA | GGT | TCC | CGC | 315 |
| Val | Asp | Gln | Asp | Leu | Val | Gly | Trp | Pro | Ala | Pro | Gln | Gly | Ser | Arg | |
| | | | | 95 | | | | | 100 | | | | | 105 | |
| TCA | TTG | ACA | CCC | TGC | ACC | TGC | GGC | TCC | TCG | GAC | CTT | TAC | CTG | GTT | 360 |
| Ser | Leu | Thr | Pro | Cys | Thr | Cys | Gly | Ser | Ser | Asp | Leu | Tyr | Leu | Val | |
| | | | | 110 | | | | | 115 | | | | | 120 | |
| ACG | AGG | CAC | GCC | GAC | GTC | ATT | CCC | GTG | CGC | CGG | CGA | GGT | GAT | AGC | 405 |
| Thr | Arg | His | Ala | Asp | Val | Ile | Pro | Val | Arg | Arg | Arg | Gly | Asp | Ser | |
| | | | | 125 | | | | | 130 | | | | | 135 | |
| AGG | GGT | AGC | CTG | CTT | TCG | CCC | CGG | CCC | ATT | TCC | TAC | CTA | AAA | GGC | 450 |
| Arg | Gly | Ser | Leu | Leu | Ser | Pro | Arg | Pro | Ile | Ser | Tyr | Leu | Lys | Gly | |
| | | | | 140 | | | | | 145 | | | | | 150 | |
| TCC | TCG | GGG | GGT | CCG | CTG | TTG | TGC | CCC | GCG | GGA | CAC | GCC | GTG | GGC | 495 |
| Ser | Ser | Gly | Gly | Pro | Leu | Leu | Cys | Pro | Ala | Gly | His | Ala | Val | Gly | |
| | | | | 155 | | | | | 160 | | | | | 165 | |
| CTA | TTC | AGG | GCC | GCG | GTG | TGC | ACC | CGT | GGA | GTG | ACC | AAG | GCG | GTG | 540 |
| Leu | Phe | Arg | Ala | Ala | Val | Cys | Thr | Arg | Gly | Val | Thr | Lys | Ala | Val | |
| | | | | 170 | | | | | 175 | | | | | 180 | |
| GAC | TTT | ATC | CCT | GTG | GAG | AAC | CTA | GAG | ACA | ACC | ATG | AGA | TCC | CCG | 585 |
| Asp | Phe | Ile | Pro | Val | Glu | Asn | Leu | Glu | Thr | Thr | Met | Arg | Ser | Pro | |
| | | | | 185 | | | | | 190 | | | | | 195 | |
| GGG | GTG | CTC | GTT | GGC | GGC | GTC | CTG | GCT | GCT | CTG | GCC | GCG | TAT | TGC | 630 |
| Gly | Val | Leu | Val | Gly | Gly | Val | Leu | Ala | Ala | Leu | Ala | Ala | Tyr | Cys | |
| | | | | 200 | | | | | 205 | | | | | 210 | |
| CTG | TCA | ACA | GGC | TGC | GTG | GTC | ATA | GTG | GGC | AGG | ATT | GTC | TTG | TCC | 675 |
| Leu | Ser | Thr | Gly | Cys | Val | Val | Ile | Val | Gly | Arg | Ile | Val | Leu | Ser | |
| | | | | 215 | | | | | 220 | | | | | 225 | |
| GGG | AAG | CCG | GCA | ATT | ATA | CCT | GAC | AGG | GAG | GTT | CTC | TAC | CAG | GAG | 720 |
| Gly | Lys | Pro | Ala | Ile | Ile | Pro | Asp | Arg | Glu | Val | Leu | Tyr | Gln | Glu | |
| | | | | 230 | | | | | 235 | | | | | 240 | |
| TTC | GAT | GAG | ATG | GAA | GAG | AAG | GAG | ACA | GAG | | | | | | 750 |
| Phe | Asp | Glu | Met | Glu | Glu | Lys | Glu | Thr | Glu | | | | | | |
| | | | | 245 | | | | | 250 | | | | | | |

(2) INFORMATION FOR SEQ ID NO:11:

(i) SEQUENCE CHARACTERISTICS:

(A) LENGTH: 18 bases
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 11:

GATCACCGGT CTAGATCT                                                     18

(2) INFORMATION FOR SEQ ID NO:12:

(i) SEQUENCE CHARACTERISTICS:
           (A) LENGTH: 28 bases
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 12:

CCGGTCCGGA AGAAAAAGAG ACGCTAGC                                          28

(2) INFORMATION FOR SEQ ID NO:13:

(i) SEQUENCE CHARACTERISTICS:
           (A) LENGTH: 79 bases
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 13:

CCGGCAATTA TACCTGACAG GGAGGTTCTC TACCAGGAAT TCGATGAGAT GGAAGAGTGC       60

CGGAAGAAAA AGAGACGCA                                                    79

(2) INFORMATION FOR SEQ ID NO:14:

(i) SEQUENCE CHARACTERISTICS:
           (A) LENGTH: 14 amino acids
           (B) TYPE: amino acid
           (C) STRANDEDNESS: single
           (D) TOPOLOGY: linear (ii) MOLECULE TYPE: polypeptide (ix) FEATURE:
           (A) NAME/KEY: NS4A Active Mutant (xi) SEQUENCE DESCRIPTION: SEQ ID NO: 14:

Gly Cys Val Val Ile Val Gly Arg Ile Val Leu Ser Gly Lys
              5                  10

(2) INFORMATION FOR SEQ ID NO:15:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: polypeptide (ix) FEATURE:
           (A) NAME/KEY: NS4A Active Mutant (xi) SEQUENCE DESCRIPTION: SEQ ID NO: 15:

Cys Val Val Ile Val Gly Arg Ile Val Leu Ser Gly Lys
              5                  10

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Soluble 5A/5B Substrate (xi) SEQUENCE DESCRIPTION: SEQ ID NO: 16:

Asp Thr Glu Asp Val Val Cys Cys Ser Met Ser Tyr Thr Trp Thr
                  5                  10                  15

Gly Lys (2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY:  Mutant 5A/5B Substrate (xi) SEQUENCE DESCRIPTION: SEQ ID NO: 17:

Asp Thr Glu Asp Val Val Ala Cys Ser Met Ser Tyr Thr Trp Thr
                  5                  10                  15

Gly (2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Mutant Soluble 5A/5B Substrate (xi) SEQUENCE DESCRIPTION: SEQ ID NO: 18:

Asp Thr Glu Asp Val Val Ala Cys Ser Met Ser Tyr Thr Trp Thr
                  5                  10                  15

Gly Lys (2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Soluble 5A/5B Substrate (xi) SEQUENCE DESCRIPTION: SEQ ID NO: 19:

```
Asp Thr Glu Asp Val Val Cys Cys Ser Met Ser Tyr Thr Trp Thr
                 5                  10                  15

Gly Lys Tyr
```

(2) INFORMATION FOR SEQ ID NO:20:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Soluble 5A/5B Substrate (xi) SEQUENCE DESCRIPTION: SEQ ID NO: 20:

```
Asp Thr Glu Asp Val Val Ala Cys Ser Met Ser Tyr Thr Trp Thr
                 5                  10                  15

Gly Lys Tyr
```

(2) INFORMATION FOR SEQ ID NO:21:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Soluble 4B/5A Substrate (xi) SEQUENCE DESCRIPTION: SEQ ID NO: 21:

```
Trp Ile Ser Ser Glu Cys Thr Thr Pro Cys Ser Gly Ser Trp Leu
                 5                  10                  15

Arg Asp Ile Trp Asp
             20
```

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: histidine tag (xi) SEQUENCE DESCRIPTION: SEQ ID NO: 22:

```
Met Arg Gly Ser His His His His His His Thr Asp Pro
                 5                  10
```

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: hydrophilic tail (xi) SEQUENCE DESCRIPTION: SEQ ID NO: 23:

Arg Lys Lys Lys Arg Arg Lys Leu Asn
                5

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: hydrophilic tail (xi) SEQUENCE DESCRIPTION: SEQ ID NO: 24:

Lys Glu Thr Glu (2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: polypeptide (ix) FEATURE:
        (A) NAME/KEY: hydrophilic tail (xi) SEQUENCE DESCRIPTION: SEQ ID NO: 25:

Trp Ile Ser Ser Glu Cys Thr Thr Pro Cys Ser Gly Ser Trp Leu
Arg Asp Ile Trp Asp
                20

(2) INFORMATION FOR SEQ ID NO:26:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: NS4A Mutant (xi) SEQUENCE DESCRIPTION: SEQ ID NO: 26:

GTG CTC GTT GGC GGC GTC CTG GCT GCT CTG GCC GCG TAT TGC CTG        45
Val Leu Val Gly Gly Val Leu Ala Ala Leu Ala Ala Tyr Cys Leu
 1               5                  10                  15

TCA ACA GGC TGC GTG GTC ATA GTG GGC AGG ATT GTC TTG TCC GGG        90
Ser Thr Gly Cys Val Val Ile Val Gly Arg Ile Val Leu Ser Gly
             20                  25                  30

AAG CCG GCA ATT ATA CCT GAC AGG GAG GTT CTC TAC CAG GAG TTC       135
Lys Pro Ala Ile Ile Pro Asp Arg Glu Val Leu Tyr Gln Glu Phe
                 35                  40                  45

GAT GAG ATG GAA GAG TGC                                           153
Asp Glu Met Glu Glu Cys
                 50

(2) INFORMATION FOR SEQ ID NO:27:

(i) SEQUENCE CHARACTERISTICS:

(A) LENGTH: 765 base pairs
(B) TYPE: nucleic acid
(C) STRANDEDNESS: single
(D) TOPOLOGY: linear (ii) MOLECULE TYPE: cDNA (ix) FEATURE:
    (A) NAME/KEY: pNB182_4AHT (xi) SEQUENCE DESCRIPTION: SEQ ID NO: 27:

```
ATG AGA GGA TCG CAT CAC CAT CAC CAT CAC ACG GAT CCG CCC ATC      45
Met Arg Gly Ser His His His His His His Thr Asp Pro Pro Ile
1               5                  10                  15

ACG GCG TAC GCC CAG CAG ACG AGA GGC CTC CTA GGG TGT ATA ATC      90
Thr Ala Tyr Ala Gln Gln Thr Arg Gly Leu Leu Gly Cys Ile Ile
                20                  25                  30

ACC AGC CTG ACT GGC CGG GAC AAA AAC CAA GTG GAG GGT GAG GTC     135
Thr Ser Leu Thr Gly Arg Asp Lys Asn Gln Val Glu Gly Glu Val
                    35                  40                  45

CAG ATC GTG TCA ACT GCT ACC CAA ACC TTC CTG GCA ACG TGC ATC     180
Gln Ile Val Ser Thr Ala Thr Gln Thr Phe Leu Ala Thr Cys Ile
                    50                  55                  60

AAT GGG GTA TGC TGG ACT GTC TAC CAC GGG GCC GGA ACG AGG ACC     225
Asn Gly Val Cys Trp Thr Val Tyr His Gly Ala Gly Thr Arg Thr
                65                  70                  75

ATC GCA TCA CCC AAG GGT CCT GTC ATC CAG ATG TAT ACC AAT GTG     270
Ile Ala Ser Pro Lys Gly Pro Val Ile Gln Met Tyr Thr Asn Val
                80                  85                  90

GAC CAA GAC CTT GTG GGC TGG CCC GCT CCT CAA GGT TCC CGC TCA     315
Asp Gln Asp Leu Val Gly Trp Pro Ala Pro Gln Gly Ser Arg Ser
                95                  100                 105

TTG ACA CCC TGC ACC TGC GGC TCC TCG GAC CTT TAC CTG GTT ACG     360
Leu Thr Pro Cys Thr Cys Gly Ser Ser Asp Leu Tyr Leu Val Thr
                110                 115                 120

AGG CAC GCC GAC GTC ATT CCC GTG CGC CGG CGA GGT GAT AGC AGG     405
Arg His Ala Asp Val Ile Pro Val Arg Arg Arg Gly Asp Ser Arg
                125                 130                 135

GGT AGC CTG CTT TCG CCC CGG CCC ATT TCC TAC CTA AAA GGC TCC     450
Gly Ser Leu Leu Ser Pro Arg Pro Ile Ser Tyr Leu Lys Gly Ser
                140                 145                 150

TCG GGG GGT CCG CTG TTG TGC CCC GCG GGA CAC GCC GTG GGC CTA     495
Ser Gly Gly Pro Leu Leu Cys Pro Ala Gly His Ala Val Gly Leu
                155                 160                 165

TTC AGG GCC GCG GTG TGC ACC CGT GGA GTG ACC AAG GCG GTG GAC     540
Phe Arg Ala Ala Val Cys Thr Arg Gly Val Thr Lys Ala Val Asp
                170                 175                 180

TTT ATC CCT GTG GAG AAC CTA GAG ACA ACC ATG AGA TCC CCG GGG     585
Phe Ile Pro Val Glu Asn Leu Glu Thr Thr Met Arg Ser Pro Gly
                185                 190                 195

GTG CTC GTT GGC GGC GTC CTG GCT GCT CTG GCC GCG TAT TGC CTG     630
Val Leu Val Gly Gly Val Leu Ala Ala Leu Ala Ala Tyr Cys Leu
                200                 205                 210

TCA ACA GGC TGC GTG GTC ATA GTG GGC AGG ATT GTC TTG TCC GGG     675
Ser Thr Gly Cys Val Val Ile Val Gly Arg Ile Val Leu Ser Gly
                215                 220                 225

AAG CCG GCA ATT ATA CCT GAC AGG GAG GTT CTC TAC CAG GAG TTC     720
Lys Pro Ala Ile Ile Pro Asp Arg Glu Val Leu Tyr Gln Glu Phe
                230                 235                 240

GAT GAG ATG GAA GAG TGC CGG AAG AAA AAG AGA CGC AAG CTT AAT     765
Asp Glu Met Glu Glu Cys Arg Lys Lys Lys Arg Arg Lys Leu Asn
                245                 250                 255
```

-continued (2) INFORMATION FOR SEQ ID NO:28:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Native NS4A (xi) SEQUENCE DESCRIPTION: SEQ ID NO: 28:

```
TCA ACA TGG GTG CTC GTT GGC GGC GTC CTG GCT GCT CTG GCC GCG  45
Ser Thr Trp Val Leu Val Gly Gly Val Leu Ala Ala Leu Ala Ala
1               5                   10                  15

TAT TGC CTG TCA ACA GGC TGC GTG GTC ATA GTG GGC AGG ATT GTC  90
Tyr Cys Leu Ser Thr Gly Cys Val Val Ile Val Gly Arg Ile Val
                20                  25                  30

TTG TCC GGG AAG CCG GCA ATT ATA CCT GAC AGG GAG GTT CTC TAC 135
Leu Ser Gly Lys Pro Ala Ile Ile Pro Asp Arg Glu Val Leu Tyr
                35                  40                  45

CAG GAG TTC GAT GAG ATG GAA GAG TGC 162
Gln Glu Phe Asp Glu Met Glu Glu Cys
                50
```

(2) INFORMATION FOR SEQ ID NO:29:

(i) SEQUENCE CHARACTERISTICS:
        (A) LENGTH: 33 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Carboxl 33 mer of NS4A (xi) SEQUENCE DESCRIPTION: SEQ ID NO: 29:

```
Cys Val Val Ile Val Gly Arg Ile Val Leu Ser Gly Lys Pro Ala
                5                   10                  15

Ile Ile Pro Asp Arg Glu Val Leu Tyr Gln Glu Phe Asp Glu Met
                20                  25                  30

Glu Glu Cys
```

(2) INFORMATION FOR SEQ ID NO:30:

(i) SEQUENCE CHARACTERISTICS:
        (A) LENGTH: 33 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Carboxl 33 mer of NS4A of HCV-BK strain (xi) SEQUENCE DESCRIPTION: SEQ ID NO: 30:

```
Ser Val Val Ile Val Gly Arg Ile Ile Leu Ser Gly Arg Pro Ala
                5                   10                  15

Ile Val Pro Asp Arg Glu Leu Leu Tyr Gln Glu Phe Asp Glu Met
                20                  25                  30

Glu Glu Cys
```

(2) INFORMATION FOR SEQ ID NO:31:

(i) SEQUENCE CHARACTERISTICS:
        (A) LENGTH: 12 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Cytomegalovirus substrate (xi) SEQUENCE DESCRIPTION: SEQ ID NO: 31:

Arg Gly Val Val Asn Ala Ser Ser Arg Leu Ala Tyr
                5                    10

(2) INFORMATION FOR SEQ ID NO:32:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Cytomegalovirus substrate (xi) SEQUENCE DESCRIPTION: SEQ ID NO: 32:

Ala Gly Val Val Ala Ser Ser Arg Leu Ala
              5                10

(2) INFORMATION FOR SEQ ID NO:33:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Cytomegalovirus substrate (xi) SEQUENCE DESCRIPTION: SEQ ID NO: 33:

Gly Val Val Asn Ala Thr Cys Arg Leu Ala
              5                10

(2) INFORMATION FOR SEQ ID NO:34:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Cytomegalovirus substrate (xi) SEQUENCE DESCRIPTION: SEQ ID NO: 34:

Gly Val Gly Asn Ala Ser Cys Arg Leu Ala
              5                10

(2) INFORMATION FOR SEQ ID NO:35:

(i) SEQUENCE CHARACTERISTICS:

(A) LENGTH: 10 amino acid residues
        (B) TYPE: amino acid
        (C) STRANDEDNESS: single
        (D) TOPOLOGY: linear (ii) MOLECULE TYPE: polypeptide (ix) FEATURE:
        (A) NAME/KEY: Cytomegalovirus substrate (xi) SEQUENCE DESCRIPTION: SEQ ID NO: 35:

Gly Val Val Asn Gly Thr Cys Arg Leu Ala
                 5                  10

(2) INFORMATION FOR SEQ ID NO:36:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: cDNA (iv) ANTI-SENSE: yes (ix) FEATURE:
        (D) OTHER INFORMATION: Antisense strand of SEQ ID NO: 11:

(xi) SEQUENCE DESCRIPTION: SEQ ID NO: 36:

TGGCCAGATC TAGA                                                             14

(2) INFORMATION FOR SEQ ID NO:37:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: cDNA (iv) ANTI-SENSE: yes (ix) FEATURE:
        (D) OTHER INFORMATION: Antisense strand of SEQ ID NO: 12:

(xi) SEQUENCE DESCRIPTION: SEQ ID NO: 37:

AGGCCTTCTT TTTCTCTGCG ATCG                                                  24

(2) INFORMATION FOR SEQ ID NO:38:

(i) SEQUENCE CHARACTERISTICS:
        (A) LENGTH: 79 bases
        (B) TYPE: nucleic acid
        (C) STRANDEDNESS: single
        (D) TOPOLOGY: linear (ii) MOLECULE TYPE: cDNA (iv) ANTI-SENSE: yes (ix) FEATURE:
        (D) OTHER INFORMATION: Antisense strand of SEQ ID NO: 13:

(xi) SEQUENCE DESCRIPTION: SEQ ID NO: 38:

GTTAATATGG ACTGTCCCTC CAAGAGATGG TCCTTAAG CT ACTCTACCTT CTCACGGCCT          60

TCTTTTTCTC TGCGTTCGA                                                        79

SURFACE PLASMON RESONANCE BASED ENZYMATIC ASSAY

This application is a continuation under 37 C.F.R. § 1.53(b) of U.S. application Ser. No. 08/440,283, filed May 12, 1995.

BACKGROUND OF THE INVENTION

High-throughput assays for screening potential inhibitors of proteases are known. An example of such an assay is the scintillation proximity assay (SPA). SPA technology involves the use of beads coated with scintillant. Bound to the beads are acceptor molecules such as antibodies, receptors or enzyme substrates which interact with ligands or enzymes in a reversible manner.

For a typical protease assay the substrate peptide is biotinylated at one end and the other end is radiolabelled with low energy emitters such as $^{125}I$ or $^3H$. The labeled substrate is then incubated with the enzyme. Avidin coated SPA beads are then added which bind to the biotin. When the substrate peptide is cleaved by the protease, the radioactive emitter is no longer in proximity to the scintillant bead and no light emission takes place. Inhibitors of the protease will leave the substrate intact and can be identified by the resulting light emission which takes place in their presence.

The SPA assay works well. However, labeling of the substrate could result in inactivation of the substrate. In addition, radiolabeled emitters may pose both health and environmental concern. Therefore there is a need for producing a high-throughput assay which does not require the use of radioactive substances.

SUMMARY OF THE INVENTION

The present invention fills this need by providing for a method for determining if a substrate is cleaved by an enzyme using surface plasmon resonance. According to the process of the present invention, the substrate and the protease are placed together in solution in a reaction vessel under conditions wherein the protease can cleave the substrate after which the reaction is stopped. The solution containing the protease and substrate are then brought into contact with a ligand bound to a sensor chip, wherein the ligand is able to bind to the substrate, and wherein the mass of the intact substrate versus the mass of the cleaved substrate is detected by surface plasmon resonance technology.

The present invention is further comprised of a method of determining if a test substance is a protease inhibitor. The test substance is placed in solution in the reaction vessel with the protease and the substrate. The solution containing the protease, substrate and test substance are then brought into contact with a ligand bound to a sensor chip, wherein the ligand is able to bind to the substrate, and wherein the mass of the substrate versus the mass of the cleaved substrate is detected by surface plasmon resonance technology. If the substrate is cleaved as determined by its decrease in mass as detected by surface plasmon resonance technology then the test substance is not a protease inhibitor. On the other hand if the substrate is a protease inhibitor, then the substrate does not have a decrease in mass as is determined by surface plasmon resonance.

BRIEF DESCRIPTION OF THE FIGURES

FIG. 8 schematically depicts a high throughput assay for determining if a substrate is cleaved by an HCV protease or discovering HCV protease inhibitors using surface plasmon resonance technology.

FIG. 8A illustrates the outcome expected in the absence of an uninhibited HCV protease, while

FIG. 9 schematically depicts a high throughput assay for determining if a substrate is cleaved by a CMV protease or discovering CMV protease inhibitors using surface plasmon resonance technology.

FIG. 9A illustrates the outcome expected in the absence of an uninhibited CMV protease, while

DETAILED DESCRIPTION OF THE INVENTION

Figure 1:
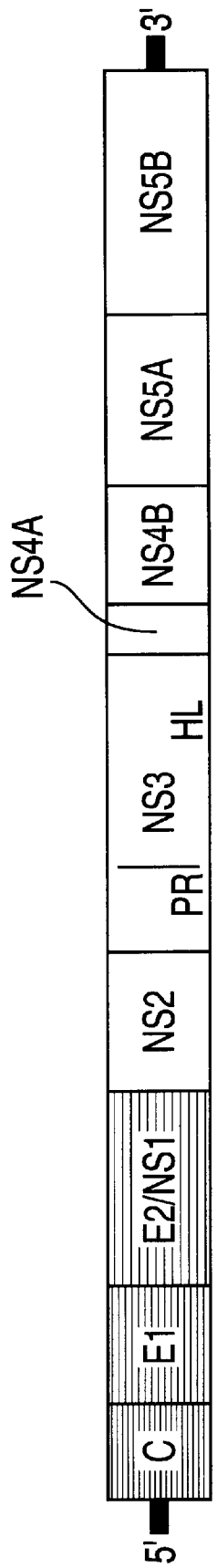
FIG. 1 schematically depicts the HCV genome.

A novel, high throughput enzymatic assay utilizing the surface plasmon resonance technology (SPR) has been successfully developed. Using this assay, and a dedicated BIAcore™ instrument, at least 1000 samples per week can be screened for either their enzymatic activity or their inhibitory effects toward the enzymatic activity, in a 96 well plate format. This methodology is readily adaptable to any enzyme-substrate reaction. We have successfully used this methodology to develop high throughput assays for CMV and HCV proteases. The advantage of this assay over the currently available SPA assay is that it does not require a radiolabeled peptide substrate.

BIAcore™ is a processing unit for Biospecific Interaction Analysis. The processing unit integrates an optical detection system with an autosampler and a microfluidic system. BIAcore™ uses the optical phenomena, surface plasmon resonance to monitor interaction between biomolecules. SPR is a resonance phenomenon between incoming photons and electrons on the surface of thin metal film. Resonance occurs at a sharply defined angle of incident light. At this angle, called the resonance angle, energy is transferred to the electrons in the metal film, resulting in a decreased intensity of the reflected light. SPR response depends on a change in refractive index in the close vicinity of the sensor chip surface, and is proportional to the mass of analyte bound to the surface. BIAcore continuously measure the resonance angle by a relative scale of resonance units (RU) and displays it as an SPR signal in a sensorgram, where RU are plotted as a function of time.

In addition, BIAcore™ uses continuous flow technology. One interactant is immobilized irreversibly on the sensor chip, comprising of a non-crosslinked carboxymethylated dextran providing a hydrophilic environment for bimolecular interaction. Solution containing the other interactant flow continuously over the sensor chip surface. As molecules from the solution bind to the immobilized ligand, the resonance angle changes resulting in a signal registered by the instrument.

In contrast to many current high throughput assays based on technologies that require radiolabeling of one of the reactants studied, in BIAcore™ no need for radiolabelling exists. This important advantage allows for development of assays for studying reactions where labeling of one of the component is either not feasible or would interfere with the true interaction of biomolecules targeted for screening.

Since the commercial availability of the BIAcore™, the surface plasmon resonance technology has been extensively and primarily been used to study the interaction of biomolecules i.e. protein-protein, protein-DNA, protein-antibody, peptide-antibody, etc. in real time. To our knowledge, there are currently no published methodologies for use of the SPR technology, specifically in a high throughput fashion for following the extent of enzyme-substrate reaction, determination of catalytic activity of enzymes, determination of enzyme kinetics and ultimately screening for inhibitors of enzymatic activity. Here, we disclose a novel methodology which when used in conjunction with SPR technology allows for rapid screening of inhibitors of enzymatic activity. In this methodology, the enzymatic reactions are carried out outside of the BIAcore, i.e. in reaction tubes or 96-well tissue culture plates, as it is conventionally done for any of the currently available high throughput assays. The SPR is only used as a detection means for determination of the amount of an intact substrate remaining in a solution with and without the enzyme after the reaction is quenched.

In order to measure the amount of the intact substrate prior to the addition of enzyme, a means of capturing the substrate onto the sensor chip had to be established. In addition, to satisfy the requirement for a high throughput assay on the BIAcore, the substrate needed to be removed from the surface subsequent to completion of analysis. This is required since the same surface will be used for the subsequent reactions. To accomplish these two requirements, a phosphotyrosine is synthetically attached to one end of the substrate. The phosphotyrosine was chosen due to the commercial availability of an anti-phosphotyrosine monoclonal antibody. The antibody is covalently attached to the sensor chip by standard amine coupling chemistry. The anti-phosphotyrosine antibody, bound permanently to the chip is used to capture the phosphotyrosine-containing substrate in a reversible manner. The antibody-phosphotyrosine interaction is ultimately used to capture and release the peptide substrate when desired by regeneration of the surface with various reagents i.e. 2 M $MgCl_2$.

Introduction of the intact peptide onto the antibody surface results in a larger mass which is detected by the instrument. To follow the extent of peptide cleavage, a mixture of peptide substrate and enzyme is incubated for the desired time and then quenched. Introduction of this mixture containing the cleaved peptide and the intact peptide to a regenerated antibody surface results in a lower mass value than that detected for a sample containing only intact peptide. The difference in the two values is then used to calculate the exact amount of intact peptide remaining after cleavage by the enzyme.

Although the reduction in mass can be directly followed with many large substrates, due to the small mass of a typical synthetic peptide substrate (10–20 amino acids, 1–3 Daltons), the mass difference, and thus the signal difference between the intact and cleaved peptide is very small within the signal to noise ratio of the instrument. To circumvent this low sensitivity, we synthesized a biotin molecule on the N-terminal of the peptide. By addition and thus tagging of peptide with streptavidin prior to injection of tagged peptide onto the antibody surface of the chip, the signal due to the presence of streptavidin will be higher. Using this approach, a cleaved peptide lacking the N-terminal half, tagged with streptavidin will result in a much lower signal.

The following examples are included to illustrate the present invention using hepatitis C protease and its substrates and the cytomegalovirus protease and its substrates.

EXAMPLES 1

Surface Plasmon Resonance Assay

The present example illustrates a method for determining if a compound can be useful as an HCV protease inhibitor using the surface plasmon resonance assay. FIGS. 8A, 8B, 9A and 9B. illustrate the technique.

Procedure for Coupling Anti-phosphotyrosine Mab to the Sensor Chip

The anti-phosphotyrosine Mab is coupled to the carboxymethylated dextran surface of a sensor chip in the following manner. The flow rate used throughout the coupling procedure is 5 $\mu$l/min. The surface is first activated with a 35 $\mu$l injection of NHS/EDC (N-hydroxysuccinimide/N-dimethyllaminopropyl-N'-ethylcarbodiimide-HCl). This is followed by a 40 ml injection of Mab 4G10 at 50 $\mu$g/ml in 10 mM sodium acetate buffer, pH=4.0. Any remaining activated esters are then blocked by the injection of 35 $\mu$l of 1 M ethanolamine. These conditions result in the immobilization of approximately 7,500 response units (420 $\mu$M) of antibody.

Binding of Peptide and Regeneration of Mab 4G10 Surface

The flow rate used throughout the BIAcore analysis run is 5 $\mu$l/min. A 4 $\mu$l injection containing streptavidin-tagged peptide (peptide concentration at 2 $\mu$M, streptavidin binding sites concentration at 9 $\mu$M) is carried out. The amount of streptavidin-tagged peptide bound to the antibody surface (in response units) is measured 30 seconds after the injection is complete.

Regeneration of sensor chip surface

Regeneration of the Mab 4G10 surface is achieved using a 4 $\mu$l pulse of 2 M $MgCl_2$ after each peptide injection. Surfaces regenerated up to 500 times still showed 100% binding of tagged peptide.

Determination of the Optimal Concentration of Peptide and Streptavidin

To determine the optimal peptide concentration, a standard curve was generated using various amounts of peptide (0–10 $\mu$M) in the presence of excess streptavidin. A value in the linear range, 2 $\mu$M, was chosen for standard assay conditions.

The amount of streptavidin required to completely tag the peptide was determined using a peptide concentration of 2.5 $\mu$M and titrating the amount of streptavidin ($\mu$M of binding sites). All the peptides were shown to be completely tagged when streptavidin concentrations greater than 3 $\mu$M (approximately equimolar to the peptide concentration) were used. A streptavidin concentration of 9 $\mu$M (a 4.5 fold excess) was chosen for standard assay conditions.

Application of Described Methodology to HCV Protease

The HCV protease 5A/5B peptide substrate, DTEDV-VACSMSYTWTGK (SEQ ID NO 18), with phosphotyrosine at the C-terminal and biotin at the N-terminal is synthesized. Anti-phosphotyrosine monoclonal antibody, 4G10 was coupled to the sensor chip.

In the absence of HCV protease, the intact streptavidin-tagged biotinylated phosphotyrosine peptide results in a large signal (large mass unit/large response units) through its interaction with the anti-phosphotyrosine monoclonal antibody.

The protease-catalyzed hydrolysis of the phosphotyrosine-biotinylated peptide was carried out in a 96 well plate. The reaction was stopped with an equal volume of the quenching buffer containing mercuribenzoate. Streptavidin was added to tag the peptide which binds to the biotin. The cleaved peptide which lacks the tagged streptavidin (less mass) results in the loss of response units.

Using this assay, numerous compounds can be tested for their inhibitory activity since the antibody surface can be regenerated repetitively with 2 M $MgCl_2$.

The peptide cleavage activity by HCV protease can be monitored in a time dependent manner using the BIAcore-based methodology. Using the concentrated enzyme and the BIAcore substrate, Biotin-DTEDVVAC SMSYTWTGK-pY (SEQ ID NO 17), 50% substrate cleavage is achieved within 1 hour using the BIAcore-based HCV assay. Based on the amount of enzyme, His-NS3(183)Δ4AHT needed to reach a 50% cleavage within 2 hours, a time scale desired for a development of a high throughput assay, we estimate that 1 liter of fermentation of the His-NS3(183)Δ4AHT construct results in enough protease to run at least 100 reactions on the BIAcore.

Standard Operating Procedure for BIAcore-based HCV Assay

Reactions are prepared in a 96-well tissue culture plate using the Reaction Buffer (50 mM HEPES, pH 7.4, 20% glycerol, 150 mM NaCl, 1 mM EDTA, 0.1% Tween-20,1 mM DTT ) as diluent. The final reaction volume is 100 μl. Sample with the peptide alone (Biotin-DTEDVVAC SMSYTWTGKpY) is prepared by addition of 10 μl of peptide stock at 100 μM (prepared in the reaction buffer) to 90 μl of reaction buffer, so that the final concentration of peptide is 10 μM. Samples comprised of peptide and the enzyme are prepared by addition of 10 μl of peptide stock at 100 μM and 10 μl of partially purified His-NS3 (183)-Δ4A-HT stock at 1.7 mg/ml (both prepared in the reaction buffer) to 80 μl of reaction buffer, so that the final concentration of peptide and the enzyme is 10 and 0.1 μM respectively. The reaction is held at 30° C. for the specified time and then quenched. Quenching is achieved by transferring a 20-μl aliquot of the reaction mixture to a new tissue culture plate containing an equal volume of PMB Quenching Buffer (50 mM HEPES, pH 7.8, 150 mM NaCl, 5 mM P-Hydroxymercuribenzoic Acid, and 13 mM EDTA).

To prepare the quenched reaction mixture for injection onto the sensor surface, 30 μl PMB BIAcore Buffer (50 mM HEPES, pH 7.4, 1 M NaCl) and 30 μl of streptavidin at 0.5 mg/ml in water is added to the 40 μl of the quenched reaction mixture to a final volume of 100 μl. In this step, all the peptides are tagged with streptavidin prior to the injection of samples. Finally, 4 μl of this sample is injected over the antiphosphotyrosine surface for determination of the intact versus cleaved peptide. The final concentration of peptide and the streptavidin in the BIAcore sample is 2 and 9 μM respectively.
Experimental Conditions:

| Substrate: | Biotin-DTEDVVAC SMSYTWTGK-pY (SEQ ID NO 19) in Reaction buffer without DTT |
|---|---|
| Concentration: | 170 μM (Crude peptide, based on weight) |
| Enzyme: | 10 μl of concentrated His-NS3 (183)-Δ4A-HT at 1.7 mg/ml |
| Reaction volume: | 100 μl |
| Reaction buffer: | 50 mM HEPES, pH 7.8 20% glycerol 150 mM NaCl 1 mM EDTA 1 mM DTT 0.1% Tween-20 |
| Temp: | 30° C. |
| Quench with: | p-hydroxymercuribenzoate |

EXAMPLE 2

Standard Operating Procedure for surface plasmon resonance CMV Assay

Reactions are prepared in a 96-well tissue culture plate using the Reaction Buffer (50 mM HEPES, pH=7.4,25% Glycerol, 1 mM DTT) as diluent. The final reaction volume is 100 μL. Sample with the peptide alone (Biotin-RGVVNA SCRLAKY (SEQ ID NO: 31) is prepared by addition of 10 μl of peptide stock at 100 mM (prepared in the reaction buffer) to 90 μl of reaction buffer, so that the final concentration of peptide is 10 μM. Samples comprised of peptide and the enzyme are prepared by addition of 10 μl of peptide stock at 100 μM and 10 μl of enzyme stock at 1 mM (both prepared in the reaction buffer) to 80 μl of reaction buffer, so that the final concentration of peptide and the enzyme is 10 and 0.1 μM respectively. The reaction is held at 25° C. for the specified time and then quenched. Quenching is achieved by transferring a 20-μl aliquot of the reaction mixture to a new tissue culture plate containing an equal volume of PMB Quenching Buffer (50 mM HEPES, pH 7.8, 150 mM NaCl, 5 mM p-Hydroxymercuribenzoic Acid, and 13 mM EDTA).

To prepare the quenched reaction mixture for injection onto the sensor surface, 30 μl PMB BIAcore Buffer (50 mM HEPES, pH 7.4, 1 M NaCl) and 30 μl of streptavidin at 0.5 mg/ml in water is added to the 40 μl of the quenched reaction mixture to a final volume of 100 μl. In this step, all the peptides are tagged with streptavidin prior to the injection of samples. Finally, 4 μl of this sample, is injected over the antiphosphotyrosine surface for determination of the intact versus cleaved peptide. The final concentration of peptide and the streptavidin in the BIAcore sample is 2 and 9 μM respectively.

Applications of Described Methodology to CMV Protease

I. Comparison of HPLC and BIAcore Methodology

A set of CMV protease reaction samples were analyzed by both standard HPLC methodology and the above described BIAcore based method. Values for the amount of intact peptide substrate remaining at each time point were determined using both methods. The extent of enzyme catalysis as measured by the BIAcore method were identical to that measured by the standard HPLC method typically used in the field of enzyme catalysis.

HPLC Substrate: A-G-V-V-N-A-S-S-R-L-A (SEQ ID NO: 32)

BIAcore Substrate: (Biotin)-R-G-V-V-N-A-S-S-R-L-A-K-(pY) (SEQ ID NO: 31)

Substrate concentration: 100 μM

Enzyme:

CMV Protease See Baum, Ellen et al., *J. Virology* January 1993 pages 497–506.

A. Refolded wild type: 0.5 μM
Time points: 10, 20, 30, 45, 70, and 100 min
Temperature: 25° C.
Reaction conditions:
  50 mM HEPES, pH 7.5
  150 mM NaCl
  1 mM DTT
  25% glycerol II. Determination of kinetic parameters for the hydrolysis of CMV maturation site substrate by various human CMV protease forms HCMV protease activity was determined by monitoring the cleavage of the peptide using the BIAcore-based methodology as described. The concentration of peptides used for the calculation of kinetics parameters was determined by amino acid composition analysis. 12 different concentrations of substrate, from 10 μM to 3.2 mM were used for $k_m$ calculation (see below). Hydrolysis at each peptide concentration was monitored at six different time points (see below). A total of 96 samples were processed in a 96 well-plate format in 12 hours for determination of kinetic parameters for each enzyme. Kinetic parameters (km, $V_{max}$, $K_{cat}$) were determined by fitting directly the velocity (initial rates at <15% of the total substrate hydrolysis) versus substrate concentration data to Michaelis-Menton equation using both BIAevaluation program (Pharmecia Biosensor) and K.cat program (BioMetallics, Inc.).
Substrate: A-G-V-V-N-A-S-S-R-L-A (SEQ ID NO: 32)
Enzyme concentration:

| CMV Protease | | |
|---|---|---|
| A. | Refolded wild type (SPA batch #35187-81): | 0.2 μM |
| B. | soluble A143V: | 0.1 μM |
| C. | soluble A143V/V209A: | 0.1 μM |

Substrate concentration: 10, 13, 16, 22, 35, 60, 110, 210, 410, 810, 1610, 3210 μM
Time points: 1, 5, 10, 15, 20, 25 min
Temperature: 22° C.
Reaction conditions:
  50 mM HEPES, pH 7.5
  150 mM NaCl
  1 mM DTT
  25% glycerol III. Validation of Enzyme Kinetics and Inhibition Determined Using BIAcore-based CMV Assay A. Effect of Enzyme Concentration and Time of Reaction on Cleavage of Native Peptide Substrate
Experimental Conditions:

| Native Peptide: | (Biotin)-R—G—V—V—N—A—S—C—R—L—A-(pY) (SEQ ID NO: 32) |
|---|---|
| Final Concentration of peptide: | 10 μM |
| Final Enzyme (A143V/V209A): | variable |
| Time course: | variable |
| Final DTT: | 1 mM |

Summary:

Using the native substrate, cleavage of the substrate is linear with respect to protease concentration (within the 0.02 to 0.08 μM range) and time (within 1 to 4 hour range). A standard BIAcore-based CMV assay using the native substrate is carried out for 2 hours at 0.06 μM resulting in 50% cleavage of the substrate.

B. Effect of Enzyme Concentration and Time of Reaction on Cleavage of P2' Serine Analog Substrate
Experimental Conditions:

| Serine analog: | (Biotin)-R—G—V—V—N—A—S—S—R—L—A-(pY) |
|---|---|
| Final Concentration of peptide: | 10 μM |
| Final Enzyme A143V/V209A): | variable |
| Time course: | variable |
| Final DTT: | 1 mM |

Summary:

Using the serine substrate, cleavage of the substrate is linear with respect to protease concentration (within the 0.1 to 0.5 μM range) and time (within 1 to 4 hour range). A standard BIAcore-based CMV assay using the serine analog is carried out for 2 hours at 0.5 μM resulting in 50% cleavage of the substrate.

C. Effect of Substrate Concentration on Rate of Hydrolysis
Experimental Conditions:

| Serine analog: | (Biotin)-R—G—V—V—N—A—S—S—R—L—A-(pY) |
|---|---|
| Final Concentration of peptide: | variable |
| Final Enzyme (A143V/V209A): | 0.1 μM |
| Time course: | 2 hours |
| Final DTT: | 1 mM |

Summary:

The rate of hydrolysis of CMV peptide substrate is linear with respect to substrate concentrations up to 60 μM. The concentration of substrate used in a standard BIAcore-based assay is 10 μM.

D. Effect of Dithiothreitol on CMV Protease Activity
Experimental Conditions:

| Serine analog: | (Biotin)-R—G—V—V—N—A—S—S—R—L—A-(pY) |
|---|---|
| Final Concentration of peptide: | 10 μM |
| Final Enzyme A(143V/V209A): | 0.5 μM |
| Time course: | variable (2 to 20 hours) |
| Final DTT | variable (0 to 1 mM) |

Protease:
1. Break cells in the presence of DTT
2. Purify supernatant on Anion Exchange Column in the presence of DTT
3. Purify protease on Phenyl Sepharose with and without DTT.

Summary

The CMV protease, purified in the absence of DTT lacks catalytic activity as judged in a 20-hour assay as compared to an active preparation, purified in the presence of DTT. Addition of DTT to the inactive protease results in a complete reactivation of the protease. Thus, presence of DTT in the CMV assay is essential for the catalytic activity of CMV protease.

E. Minimum Requirement of DTT for CMV Protease Activity

Experimental Conditions:

A stock preparation of CMV protease, purified entirely in the presence of DTT, and subsequently stored with DTT (final concentration=2 mM) was used. For the assay, titration of DTT from 800 μM down to 4 μM was carried out so that the final concentration of enzyme in all reaction was 0.04 μM. All reactions were stopped at various times (1, 2, 3, and 4 hours) by addition of equal volume of 5 mM mercuribenzoate.

| | |
|---|---|
| Native Peptide: | (Biotin)-R—G—V—V—N—A—S—C—R—L—A-(pY) |
| Final Concentration of peptide: | 10 μM |
| Final Enzyme A143V/V209A): | 0.04 μM |
| Time course: | variable (1–4 hours) |
| Final DTT: | variable (4–800 μM) |
| Final free SH (enzyme and substrate) | 10.2 μM |

Summary:

A 200-fold reduction of DTT concentration from 800 μM to 4 μM lowers the percent cleavage of the native substrate by only 12% at 2 hours, a time period for a standard BIAcore assay resulting in a 50% cleavage of the substrate. This reduction in percent cleavage can easily be recovered by increasing the time of the reaction from 2 to 3 hours. Thus currently, the BIAcore based CMV assay can be carried out at DTT concentration as low as 4 μM. By increasing the time of the reaction, concentration of DTT may further be lowered if desired.

F. CMV Protease Inhibition Study with Compound 33277-129-2 assayed in the presence of 4 and 800 μM DTT using BIAcore-based CMV Assay Experimental Conditions:

| | |
|---|---|
| Native Peptide: | (Biotin)-R—G—V—V—N—A—S—C—R—L—A-(pY) |
| Final Concentration of peptide: | 10 μM |
| Final Enzyme (A143V/V209A): | 0.04 μM |
| Time course: | variable (1–4 hours) |
| Final DTT: | 4 μM or 800 μM |
| Compound: | 33277-129-2 (Stock: 5.8 mM in 100% DMSO) |
| Final concentration of compound: | 12 or 116 μM |
| Final DMSO: | 2% |
| Incubation: | Preincubate compound with protease for 30 min; Add substrate; Incubate for 1–4 hours; Stop reaction. |

Summary:

The compound 33277-129-2 is shown to inhibit the CMV protease activity by 40% at ~12 μM and 60% at ~100 μM in the presence of 4 μM DTT. The percent inhibition by this compound is lowered to 33% at 12 μM and 40% at 100 μM in the presence of 800 mM DTT.

IV. Competitive Inhibition of CMV Protease Activity by Maturation Site Peptide Analogs Monitored on BIAcore The apparent affinity (km) of the purified double mutant form of CMV protease, A143V/V209A for the maturation site peptide, AGVVNA$\underline{S}$RLA (P2' serine analog) was determined to be 900 μM at 22° C. using the BIAcore-based CMV assay (Table 1).

Various analogs of this substrate were then characterized in order to further define the amino acids crucial for hydrolysis versus those involved in enzyme binding. To address this issue, the interaction of native maturation site peptide (GVVNASCRLA) and four of its mutant analogs with the enzyme were studied by both directly monitoring the hydrolysis of each peptide by the enzyme on the HPLC, and the competition of each peptide with the biotinylated native substrate using the CMV assay developed on the BIAcore.

The HPLC results indicate that three out of four analogs tested (analogs A, C, D) were not hydrolyzed by the enzyme as monitored on HPLC. Two of the three non-hydrolyzable peptides (analogs A, D) were synthesized with only a single amino acid mutation where as analog C was synthesized so two of its amino acids were mutated to two non-native amino acids.

The mechanism behind the loss of hydrolysis for analog A and C versus analog D was deciphered by the competition studies carried out using the BIAcore-based CMV assay. The results of this assay show that the peptide substrate analogs A and C retain their binding ability to the enzyme but they are not hydrolyzed. These peptides inhibited the enzyme activity by competing with the biotinylated native substrate with a similar IC-50 to that of the native peptide (IC-50$_{native}$ ~1 mM; IC-50$_{mutants}$ ~1.5 mM). On the other hand, the results of the competition assay indicate that the lack of any observed hydrolysis for the peptide substrate analog D (as monitored on HPLC) is due to the loss of its binding ability to the enzyme as this peptide is not capable of competing with the biotinylated native peptide as detected on the BIAcore.

TABLE 1

APPARENT KINETIC PARAMETERS FOR THE VARIOUS RECOMBINANT HUMAN CMV PROTEASE CONSTRUCTS WITH THE MATURATION SITE PEPTIDE AGVVNASSRLA

| CMV Protease | $K_m$ (μM) | $k_{cat}$ (min$^{-1}$) | $k_{cat}/K_m$ (min$^{-1}$ · μM$^{-1}$) |
|---|---|---|---|
| Refolded Wild Type | 1023 ± 123 | 56 | 0.055 |
| A143V Mutant | 962 ± 107 | 63 | 0.066 |
| A143V/V209A Mutant | 893 ± 99 | 73 | 0.082 |

EXAMPLE 3

Production of HCV NS3 Protease

A. Plasmid constructions.

Figure 2:
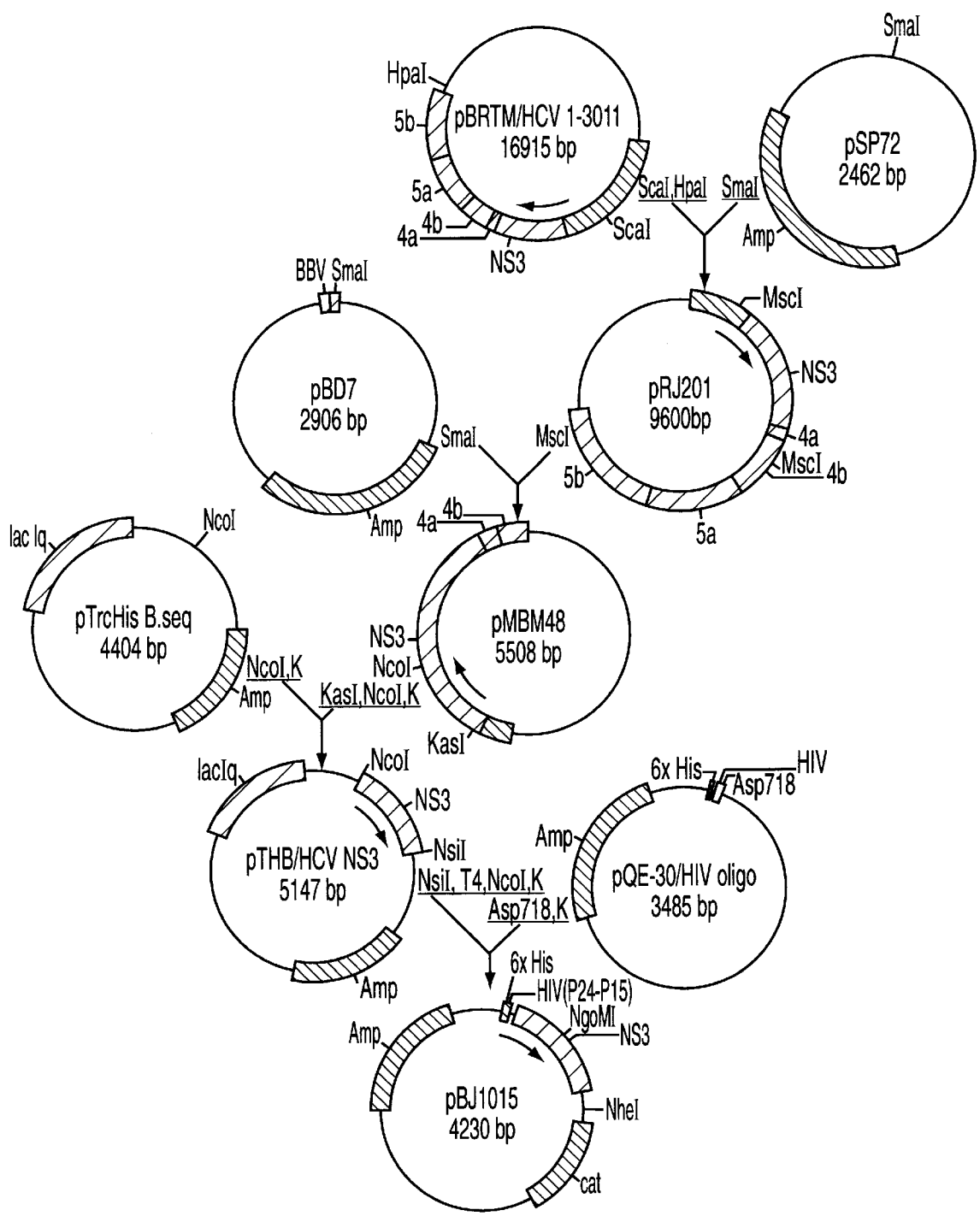
FIG. 2 depicts the recombinant synthesis of plasmid pBJ1015.
Figure 3:
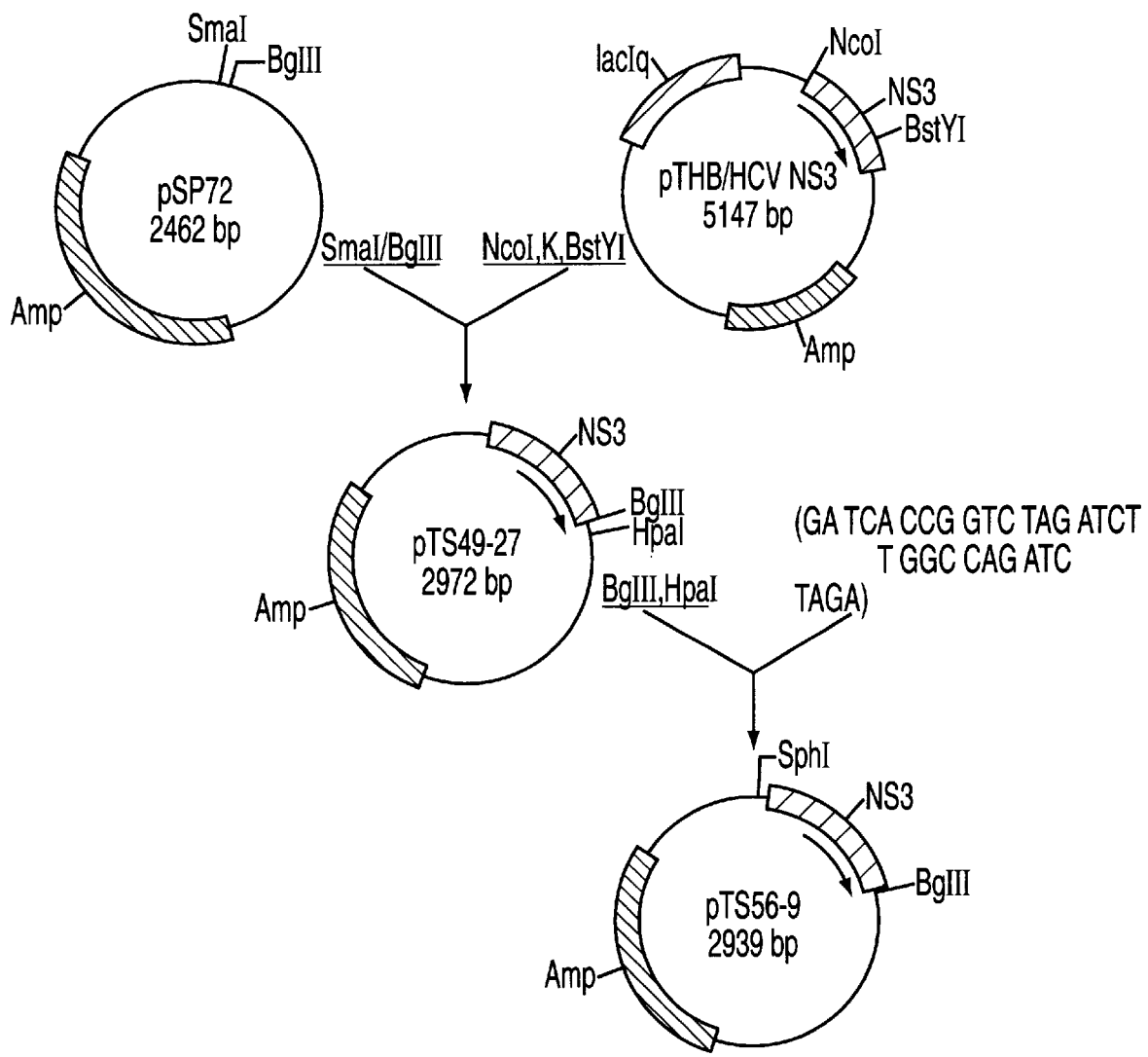
FIG. 3 depicts the recombinant synthesis of plasmid pTS56-9.

Several plasmids were designed and constructed using standard recombinant DNA techniques (Sambrook,Fritsch & Maniatis) to express the HCV protease in *E. coli* (FIG. 2–7). All HCV specific sequences originated from the parental plasmid pBRTM/HCV 1-3011 (Grakoui et al.1993). To express the N-terminal 183 amino acid versions of the protease, a stop codon was inserted into the HCV genome using synthetic oligonucleotides (FIG. 3). The plasmids designed to express the N-terminal 246 amino acid residues were generated by the natural Nco1 restriction site at the C-terminus.

i) Construction of the plasmid pBJ1015 (FIG. 2)

The plasmid pBRTM/HCV 1-3011 containing the entire HCV genome (Grakoui A., et al., *J. Virol.* 67: 1385–1395) was digested with the restriction enzymes Sca I and Hpa I and the 7138 bp (base pair) DNA fragment was isolated and cloned to the Sma I site of pSP72 (Promega) to produce the plasmid, pRJ201. The plasmid pRJ 201 was digested with Msc I and the 2106 bp Msc I fragment was isolated and cloned into the Sma I site of the plasmid pBD7. The resulting plasmid pMBM48 was digested with Kas I and Nco I, and the 734 bp DNA fragment after blunt ending with Klenow polymerase was isolated and cloned into Nco I digested, klenow polymerase treated pTrc HIS B seq expression plasmid (Invitrogen). The ligation regenerated a Nco I site at the 5' end and Nsi I site at the 3' end of HCV sequence. The plasmid pTHB HCV NS3 was then digested with Nco I and Nsi I, and treated with klenow polymerase and T4 DNA polymerase, to produce a blunt ended 738 bp DNA fragment which was isolated and cloned into Asp I cut, klenow polymerase treated expression plasmid pQE30 (HIV). The resulting plasmid pBJ 1015 expresses HCV NS3 (246 amino acids) protease.

(ii) Construction of the plasmid pTS 56-9 with a stop codon after amino acid 183 (FIG. 3)

The plasmid pTHB HCV NS3 was digested with Nco I, treated with klenow polymerase, then digested with Bst Y I; and the DNA fragment containing HCV sequence was isolated and cloned into Sma I and Bgl II digested pSP72. The resulting plasmid pTS 49-27 was then digested with Bgl II and Hpa I and ligated with a double stranded oligonucleotide:

```
           CCG GCA  ATT ATA CCT GAC AGG GAG GTT CTC TAC CAG GAA TTC (SEQ ID NO 13)
               GT  TAA TAT GGA CTG TCC CTC CAA GAG ATG GTC CTT AAG

GAT GAG ATG GAA GAG TGC CGG AAG AAA  AAG AGA CGC A
           CTA CTC TAC CTT CTC ACG GCC TTC TTT  TTC TCT GCG TTC GA

GA TCA CCG GTC TAG ATCT     (SEQ ID NO 11)
       T CGC CAG ATC TAGA
``` to produce pTS 56-9.

Thus, a stop codon was placed directly at the end of DNA encoding the protease catalytic domain of the NS3 protein. This enabled the HCV protease to be expressed independently from the helicase domain of the NS3 protein.

Figure 4:
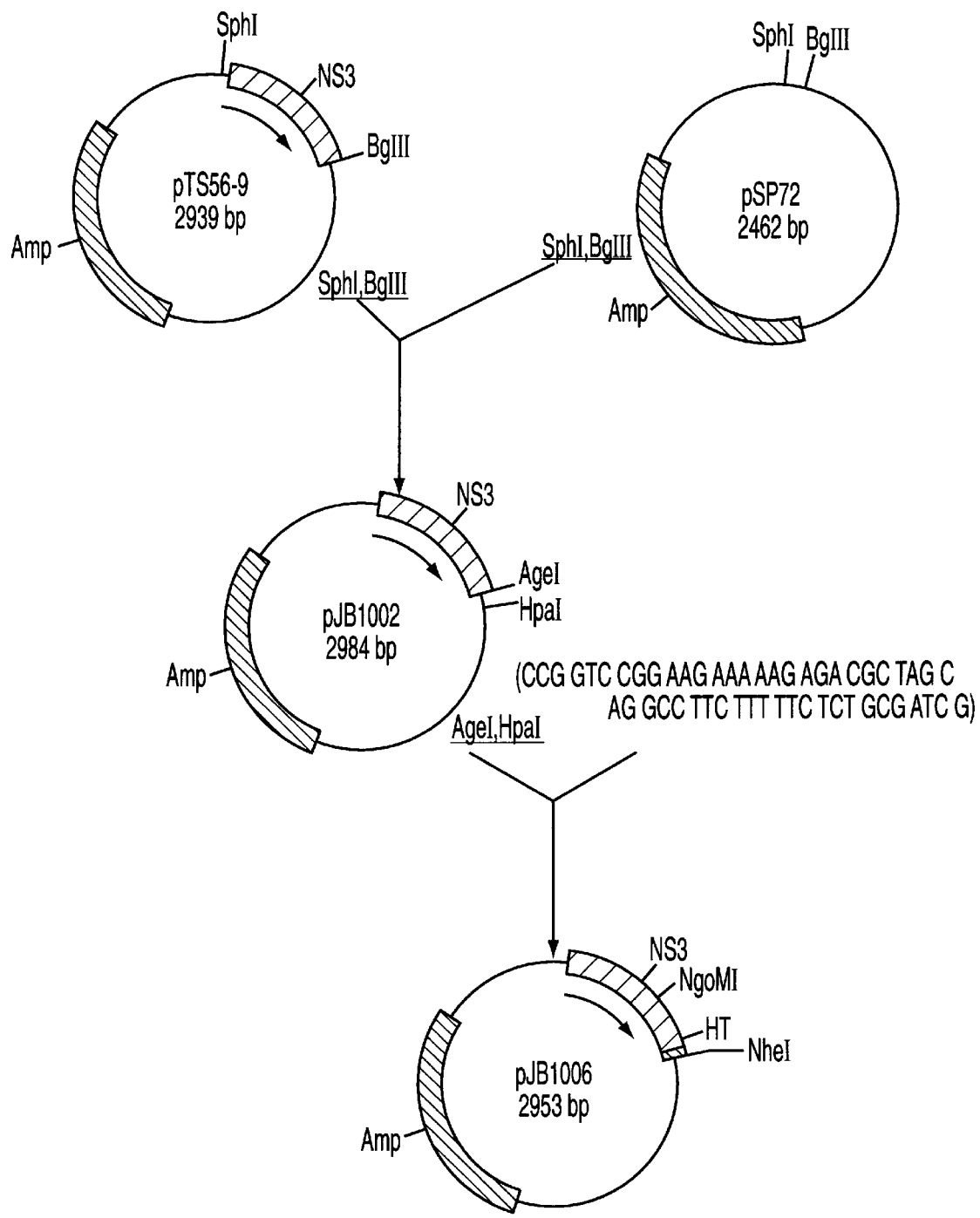
FIG. 4 depicts the recombinant synthesis of plasmid pJB1006.

(iii) Construction of the plasmid pjB 1006 Fused with a peptide of positively charged amino acids at the carboxy terminus of NS3 183 (FIG. 4).

The plasmid pTS 56-9 was digested with Sph I and Bgl II and the DNA fragment containing HCV sequence was isolated and cloned into a Sph I, Bgl II cut pSP72. The resulting plasmid pJB 1002 digested with Age I and HpaI and ligated to a double stranded oligonucleotide,

```
                                              (SEQ ID NO 12),
    CCG GTC CGG AAG AAA AAG AGA CGC TAG C
        AG GCC TTC TTT TTC TCT GCG ATC G
``` to construct pJB 1006. This fused the hydrophilic, solubilizing motif onto the NS3 protease.

Figure 5:
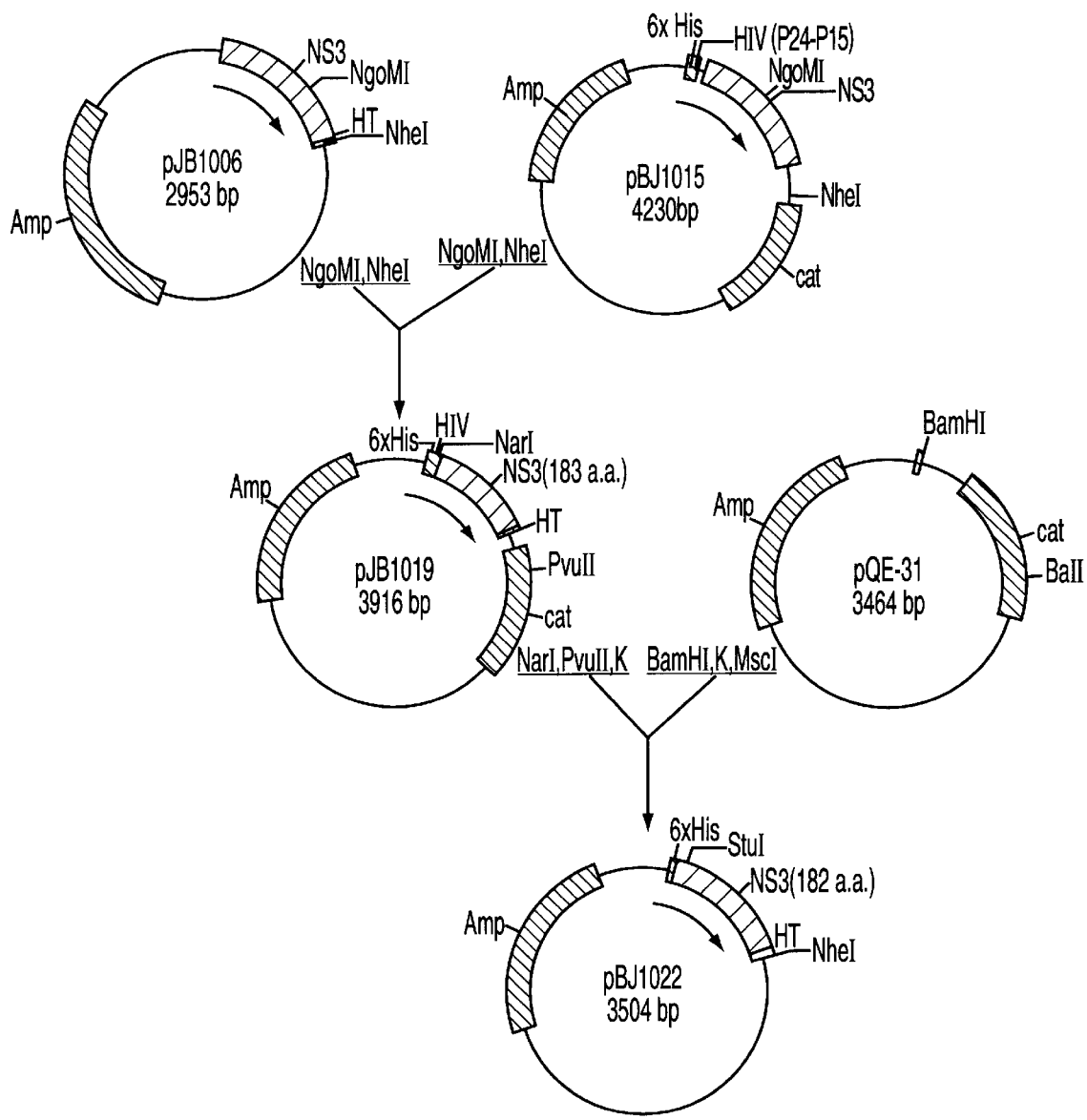
FIG. 5 depicts the recombinant synthesis of plasmid pBJ1022.

(iv) Construction of the plasmid pBJ 1022 expressing His-NS3(183)-HT in E.coli (FIG. 5)

The plasmid pJB 1006 was digested with NgoM I and Nhe I and the 216 bp DNA fragment was isolated and cloned into Ngo M I, Nhe I cut pBJ 1015 to construct plasmid pBJ 1019. The plasmid pBJ 1019 was digested with Nar I and Pvu II, and treated with Klenow polymerase to fill in 5' ends of Nar I fragments. The expression plasmid pQE31 (Invitrogen) was digested with BamH I, blunt ended with Klenow polymerase. The 717 bp Nar I- Pvu II DNA fragment was isolated and ligated to the 2787 bp BamH I/Klenowed—Msc I (Bal I) fragment of the expression plasmid pQE31 (Invitrogen). The recombinant plasmid, pBJ 1022, obtained after transformation into E.coli expresses His NS3(2-183)-HT which does not contain any HIV protease cleavage site sequence. The plasmid also contains a large deletion in the CAT (Chloramphenicol Acetyl Transferase) gene.

Figure 6:
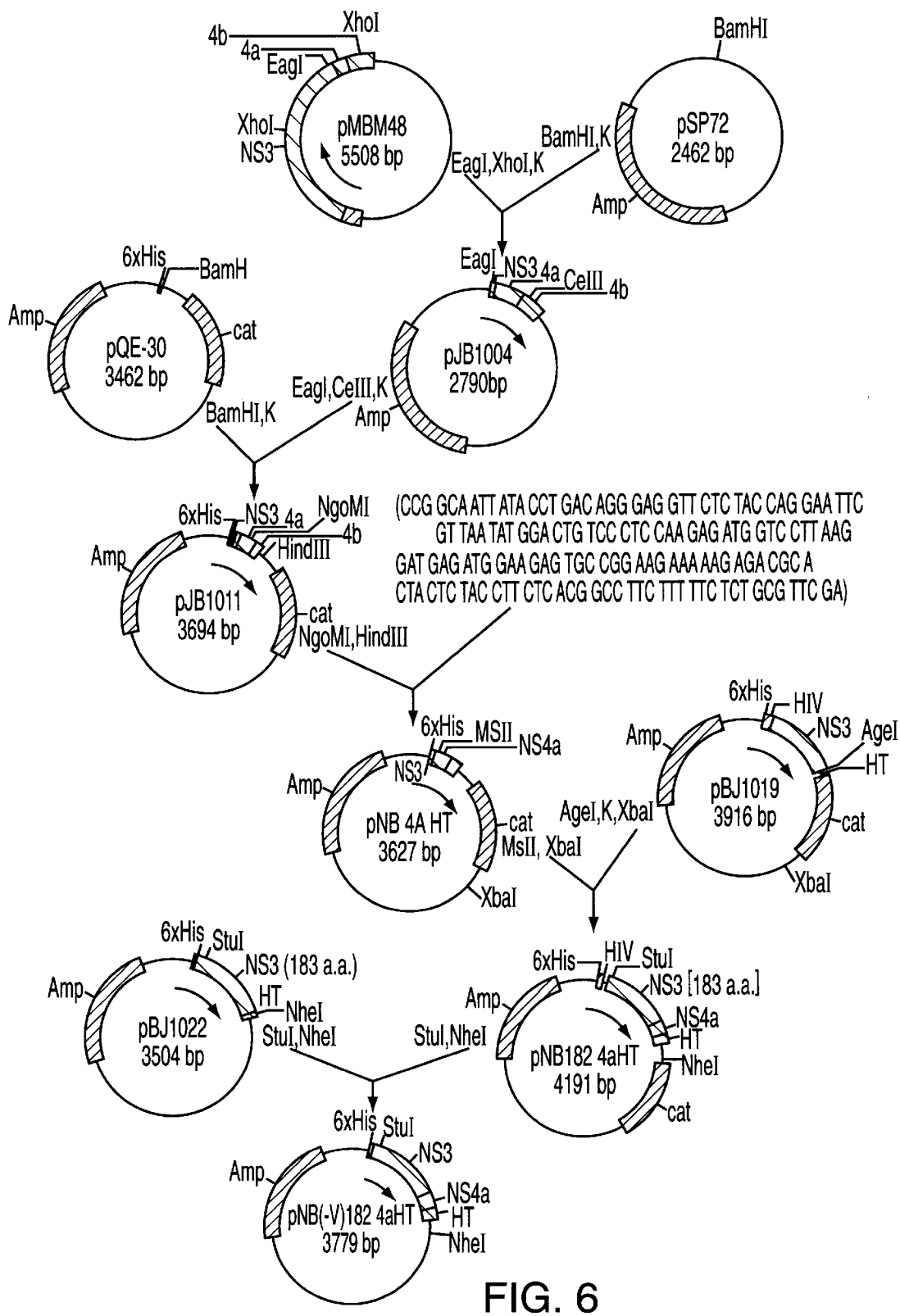
FIG. 6 depicts the recombinant synthesis of plasmid pNB(-V)182Δ4AHT.

(v) Construction of the plasmid pNB(-V)182-Δ4A HT (FIG. 6)

The plasmid pMBM 48 was digested with Eag I and Xho I, treated with Klenow polymerase and the 320 bp DNA fragment was isolated and cloned into BamH I cut, blunt ended pSP 72 to construct the plasmid pJB1004. The 320 bp fragment encodes 7 amino acid from carboxy terminal of NS3(631), all of NS4A, and the amino terminal 46 amino acid of NS4B. The recombinant plasmid pJB1004 was digested with Eag I and Cel 2, blunt ended with Klenow polymerase. The 220 bp DNA fragment was isolated and cloned into the expression plasmid pQE30 which was digested with BamH I and blunt ended with Klenow polymerase prior to ligation. The resulting plasmid pJB 1011 was digested with NgoM I and Hind III and ligated to a double stranded oligonucleotide, to construct the plasmid pNB 4A HT. The plasmid pNB 4AHT was digested with Msl I and Xba I. The 1218 bp DNA fragment was isolated and cloned into Age I cut, klenow polymerase treated, Xba I cut vector DNA of pBJ 1019. The ligation results in a substitution of the 183rd amino acid residue valine by a glycine residue in NS3, and a deletion of amino terminal three amino acid residues of NS4A at the junction. The recombinant plasmid pNB182Δ4A HT comprising NS3(182aa)-G-NS4A(4-54 amino acid) does not contain NS3/NS4A cleavage site sequence at the junction and is not cleaved by the autocatalytic activity of NS3. Finally the plasmid pNB182Δ4A HT (SEQ ID NO 8) was digested with Stu I and Nhe I, the 803 bp DNA fragment was isolated and cloned into Stu I and Nhe I cut plasmid pBJ 1022. The resulting plasmid pNB(-V)182-Δ4A HT contains a deletion of the HIV sequence from the amino terminus end of the NS3 sequence and in the CAT gene (SEQ ID NO 27).

Figure 7:
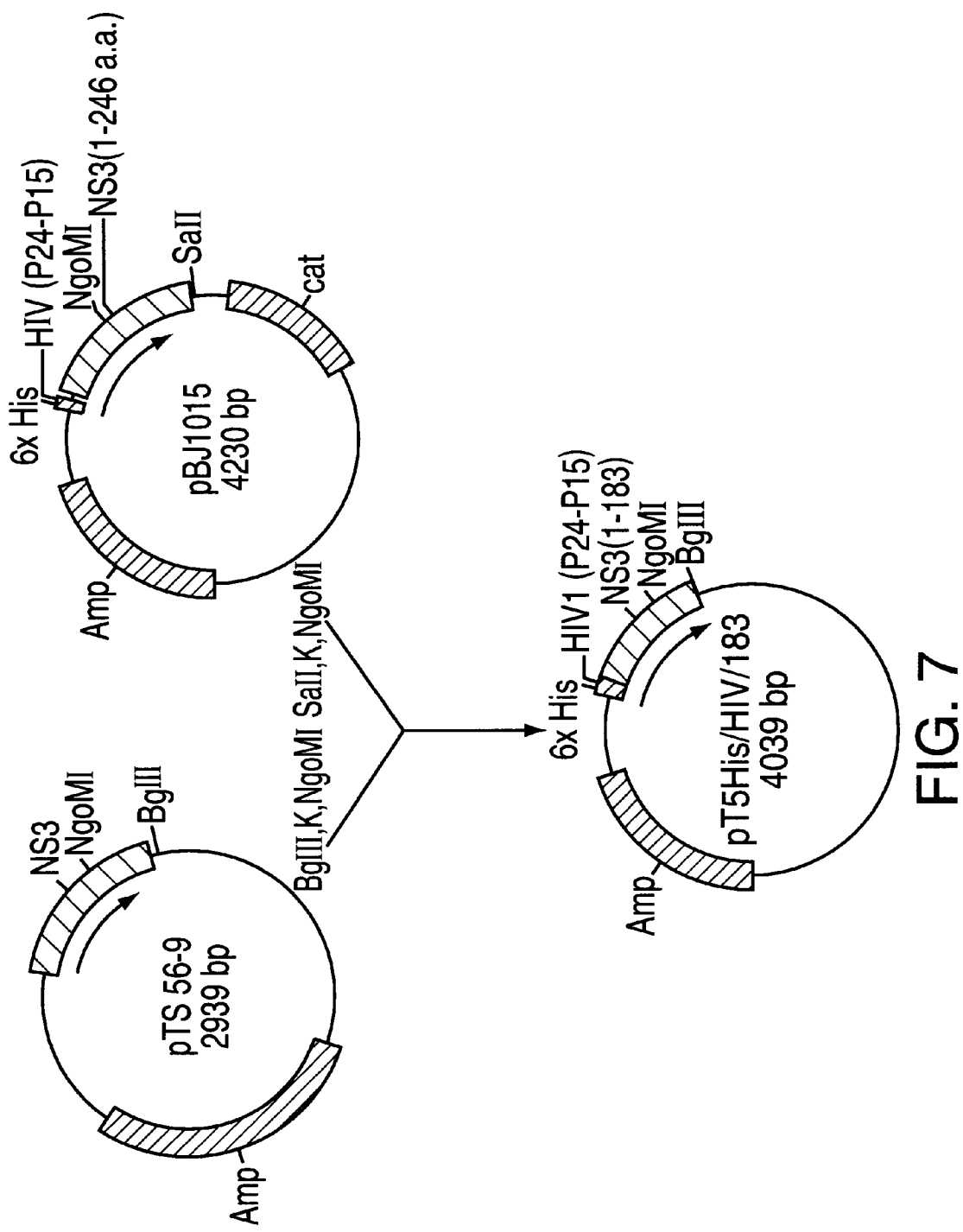
FIG. 7 depicts the recombinant synthesis of plasmid pT5His/HIV/183.
Figure 8A:
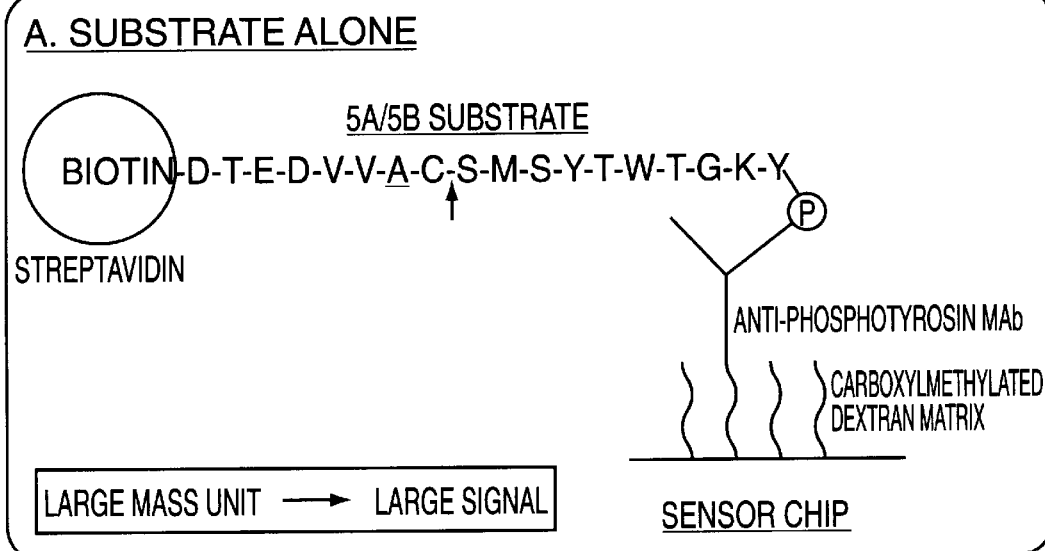
Figure 8B:
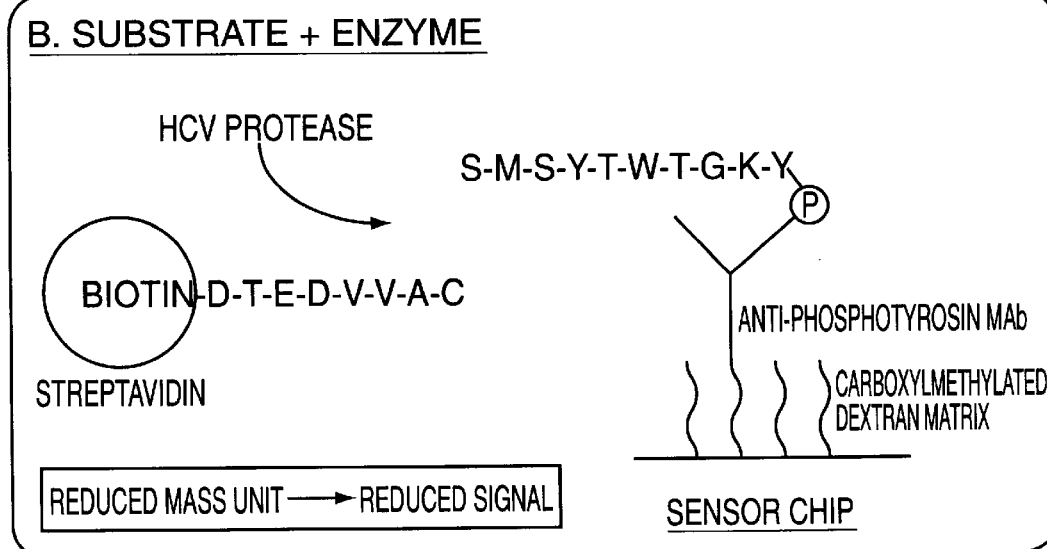
FIG. 8B illustrates the outcome expected in the presence of an active HCV protease.
Figure 9A:
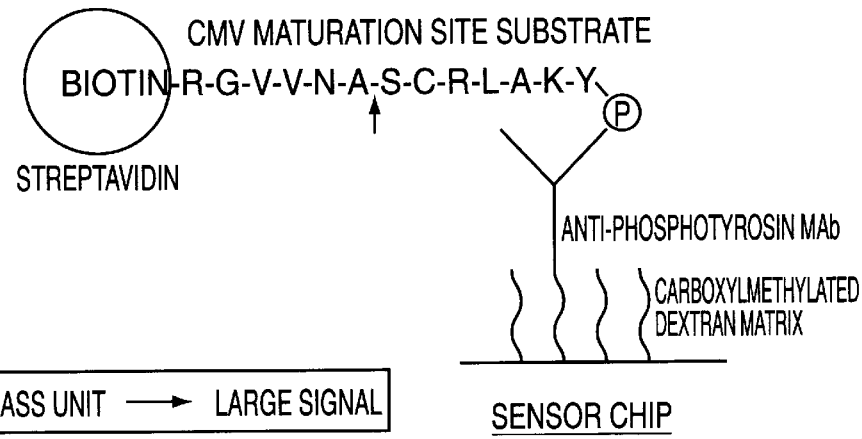
Figure 9B:
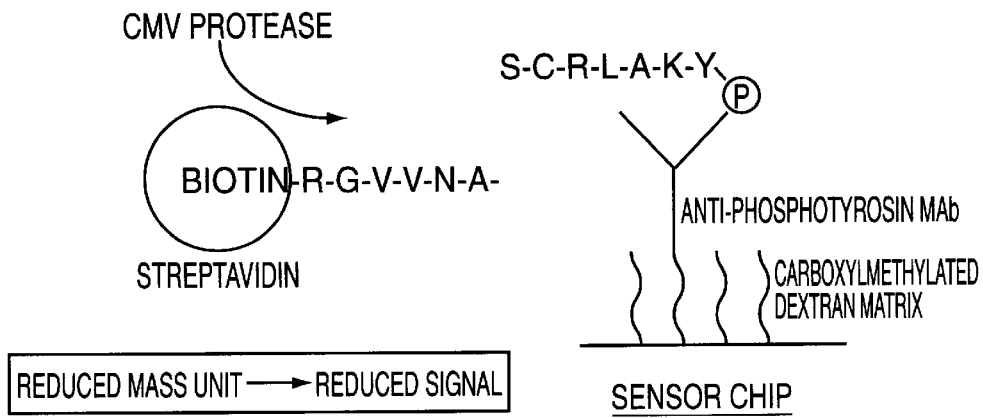
FIG. 9B illustrates the outcome expected in the presence of an active CMV protease.

(vi) Construction of the plasmid pT5 His HIV-NS3 (FIG. 7)

The plasmid pTS56-9 was digested with Bgl II, and treated with Klenow polymerase to fill in 5' ends. The plasmid was then digested with NgoM I and the blunt ended Bgl II/NgoMI fragment containing the NS3 sequence was isolated and ligated to the SglI, Klenow treated NgmMI cut and Sal I klenowed pBJ 1015. The resulting plasmid is designated pT5His HIV 183.

EXAMPLE 4

Purification of HCV NS3 Protease having a Solubilizing Motif

Purification of His182HT (SEQ ID NO 4) and His (-V) 182Δ4AHT (SEO ID NO 8)

The recombinant plasmids pBJ1022 and pNB(-V) 182Δ4A were used to transform separate cultures of E. coli strain M15 [pREP4] (Qiagen), which over-expresses the lac repressor, according to methods recommended by the manufacturer. M15 [pREP4] bacteria harboring recombinant plasmids were grown overnight in broth containing 20 g/L bactotrypton, 5 g/L bacto-yeast extract, 10 g/L NaCl and supplemented with 100 μg/ml ampicillin and 25 μg/ml kanamycin. Cultures were diluted down to O.D.600 of 0.1, then grown at 30° C. to O.D.600 of 0.6 to 0.8, after which IPTG was added to a final concentration of 1 mM. At post-induction 2 to 3 hours, the cells were harvested by pelleting, and the cell pellets were washed with 100 mM Tris, pH 7.5. Cell lysates were prepared as follows: to each ml equivalent of pelleted fermentation broth was added 50 μl sonication buffer (50 mM sodium phosphate, pH 7.8, 0.3M NaCl) with 1 mg/ml lysozyme; cell suspension was placed on ice for 30 min. Suspension was then brought to a final concentration of 0.2% Tween-20, 10 mM dithiothreitol (DTT), and sonicated until cell breakage was complete. Insoluble material was pelleted at 12,000×g in a microcentrifuge for 15 minutes, the soluble portion was removed to a separate tube and the soluble lysate was then brought to a final concentration of 10% glycerol. Soluble lysates from cells expressing the plasmids produce strongly immunoreactive bands of the predicted molecular weight. Soluble lysates prepared for $Ni^{2+}$ column purification were prepared with 10 mM β-mercaptoethanol (BME) instead of DTT. Lysates were stored at −80° C.

Purification using $Ni^{2+}$-Nitrosyl acetic acid (NTA) agarose (QIAGEN)

The proteins were then purified by placing the extracted lysate on an NTA agarose column. NTA agarose column chromatography was used because the histidine tag which was fused to the N-terminus of the proteases readily binds to the nickel column. This produces a powerful affinity chromatographic technique for rapidly purifying the soluble protease. The column chromatography was performed in a batch mode. The $Ni^{2+}$ NTA resin (3 ml) was washed twice with 50 ml of Buffer A (50 mM sodium phosphate pH 7.8 containing 10% glycerol, 0.2% Tween-20, 10 mM BME). The lysate obtained from a 250 ml fermentation (12.5 ml) was incubated with the resin for one hour at 4° C. The flow through was collected by centrifugation. The resin was packed into a 1.0×4 cm column and washed with buffer A until the baseline was reached. The bound protein was then eluted with a 20 ml gradient of imidazole (0–0.5M) in buffer A. Eluted fractions were evaluated by SDS-PAGE and western blot analysis using a rabbit polyclonal antibody to His-HIV 183.

Purification using POROS metal-chelate affinity column

In an alternative method to purify the proteins the lysate containing the proteins were applied to a POROS metal-chelate affinity column. Perfusion chromatography was performed on a POROS MC metal chelate column (4.6×50 mm, 1.7 ml) precharged with $Ni^{2+}$. The sample was applied at 10 ml/min and the column was washed with buffer A. The column was step eluted with ten column volumes of buffer A containing 25 mM imidazole. The column was further eluted with a 25 column volume gradient of 25–250 mM imidazole in buffer A. All eluted fractions were evaluated by SDS-PAGE and western blot analysis using rabbit polyclonal antibody.

EXAMPLE 5

Peptide Synthesis of the 5A/5B and 4B/5A Substrates

The peptides 5A/5B and 4B/5A substrates (SEQ ID NOs 16, 18, 19, 20 and 21) were synthesized using Fmoc chemistry on an ABI model 431A peptide synthesizer. The manufacture recommended FastMoc™ activation strategy (HBTU/HOBt) was used for the synthesis of 4A activator peptide. A more powerful activator, HATU with or without the additive HOAt were employed to assemble 5A/5B substrate peptides on a preloaded Wang resin. The peptides were cleaved off the resin and deprotected by standard TFA cleavage protocol. The peptides were purified on reverse phase HPLC and confirmed by mass spectrometric analysis.

EXAMPLE 6

HPLC-assay using a synthetic 5A/5B peptide substrate

To test the proteolytic activity of the HCV NS3 protease the DTEDVVCC SMSYTWTGK (SEQ ID NO 16) and soluble HCV NS3 (SEQ ID NO 27) were placed together in an assay buffer. The assay buffer was 50 mM sodium phosphate pH 7.8, containing 15% glycerol, 10 mM DTT, 0.2% Tween20 and 200 mM NaCl). The protease activity of SEQ ID NO 27 cleaved the substrate into two byproduct peptides, namely 5A and 5B. The substrate and two byproduct peptides were separated on a reversed-phase HPLC column. (Dynamax, 4.6×250 mm) with a pore size of 300 Å and a particle size of 5 μm. The column was equilibrated with 0.1% TFA (Solvent A) at a flow rate of 1 ml per minute. The substrate and the product peptide standards were applied to the column equilibrated in A. Elution was performed with a acetonitrile gradient (Solvent B=100% acetonitrile in A). Two gradients were used for elution (5% to 70% B in 50 minutes followed by 70% to 100% B in 10 minutes).

In another experiment, partially purified SEQ ID NO 27 or vector control was incubated with 100 μM of substrate for 3, 7 and 24 hours at 30° C. The reaction mixture was quenched by the addition of TFA to 0.01% and applied to the reversed-phase HPLC column. The fractions from each run were evaluated by mass spectrometry and sequencing.

EXAMPLE 7

Refolding of Insoluble HCV NS3 Protease

The present example describes a novel process for the refolding of HCV NS3 protease which does not have a solubilizing motif from an *E.coli* inclusion body pellet. This procedure can be used to generate purified enzyme for activity assays and structural studies.

Extraction and Purification of His-HIV 183 from the *E.coli* inclusion body pellet

*E. coli* cells harboring the plasmid for HisHIV183 was used to transform a culture of *E. coli* strain M15 [pREP] (Qiagen), which over-expresses the lac repressor, according to methods recommended by commercial source. M15 [pREP] bacteria harboring recombinant plasmids were grown overnight in 20-10-5 broth supplemented with 100 μg/ml ampicillin and 25 μg/ml kanamycin. Cultures were diluted to O.D.600 of 0.1, then grown at 37° C. to O.D.600 of 0.6 to 0.8, after which IPTG was added to a final concentration of 1 mM. At post-induction 2 to 3 hours, the cells were harvested by pelleting, and the cell pellets were washed with 100 mM Tris, pH 7.5. were pelleted by centrifugation. The cell pellet was resuspended in 10 ml of 0.1M Tris-HCl, 5 mM EDTA, pH 8.0 (Buffer A) for each gm wet weight of pellet. The pellet was homogenized and resuspended using a Dounce homogenizer. The suspension was clarified by centrifugation at 20,000×g for 30 minutes at 4° C. The pellet was sequentially washed with the following five buffers:

1. Buffer A
2. 1.0M sodium chloride (NaCl) in buffer A
3. 1.0% Triton X-100 in buffer A
4. Buffer A
5. 1.0 M Guanidine HCl (GuHCl) in buffer A.

The washed pellet was solubilized with 5M GuHCl, 1% beta mercaptoethanol in buffer A (3 ml per gm wet wt. of pellet) using a Dounce homogenizer and centrifuged at 100,000×g for 30 minutes at 4° C. Purification of denatured HisHIV183 from high molecular weight aggregates was accomplished by size exclusion on a SEPHACRYL S-300 gel filtration column.

In particular, an 8 ml sample of the 5.0M GuHCl *E. coli* extract was applied to a 160 ml Pharmacia S-300 column (1.6×100 cm) at a flow rate of 1.0 ml/min. The column buffer was comprised of 5.0 M GuHCl, 0.1 M Tris-HCl, pH 8.0, and 5.0 mM EDTA. The fraction size was 5.0 ml.

Appropriate fractions were pooled based on the results of SDS-PAGE, as well as N-terminal sequence analysis of the protein transferred to a Pro-Blot.

Detergent-assisted refolding of HCV-protease

The protein was concentrated by ultrafiltration using a 43 mm Amicon YM10 membrane to 1.0 mg per ml in 5M GuHCl, 0.1M Tris-HCl pH 8.0, 1.0 mM EDTA, 1.0% beta-mercaptoethanol. It was then diluted 50-fold to 0.1M GuHCl in refolding buffer (100 mM sodium phosphate pH 8.0, 10 mM DTT, 0.1% lauryl maltoside) and the mixture was incubated on ice for at least one hour. A 25 ml sample containing 500 μg of the protein in the refolding buffer was applied to a Pro-RPC HR 3/5 reversed phase chromatography column. The applied sample contained 500 μg protein in 25 ml of refolding buffer. To the column was then applied a solution B comprised of 99.9% $H_2O$+0.1% trifluoroacetic acid (TFA). A 10 ml volume of solution C [10% $H_2O$, 90% acetonitrile (AcN)+0.1% TFA] was applied to the column at a 0–60% gradient into solution B at a flow rate of 0.5 ml/min. and a fraction size of 0.5 ml. The fractions were monitored at A214; 2.0 absorbance units full scale (AUFS).

Fractions containing the protein (corresponding to peak 1) were pooled for renaturation by stepwise dialysis. The fractions were first dialysed in 0.1% TFA in 25% glycerol overnight at 4° C.; then dialyzed in 0.01% TFA in 25% glycerol overnight at 4° C.; then dialyzed in 0.001% TFA in 25% glycerol for 3.0 hours; then dialyzed for 3 hours at 4° C. in 50 mM $NaPO_4$, pH 6.0, 10 mM dithiotreitol (DTT) in 25% glycerol. The protein was then dialyzed for 3.0 hours at 4° C. in 50 mM $NaPO_4$, pH 7.0, 0.15 M NaCl, 10 mM DTT in 25% glycerol; and then finally dialyzed in 50 mM $NaPO_4$, pH 7.8, 0.3 M NaCl, 10 mM DTT, 0.2% Tween 20 in 25% glycerol. This resulted in purified, refolded, soluble, active HCV NS3 protease.

Far UV circular dichroism (CD) analysis of the protein was used to monitor the refolding from an acid denatured state to a folded state at neutral pH. The protein recovery was monitored by a UV scan and SDS-PAGE analysis.

Results:

Detergent-assisted Refolding of His-HIV183

HisHIV183 was quantitatively extracted from an *E. coli* inclusion body pellet. SDS-PAGE analysis at the various stages of extraction shows that sequential washes are essential to remove significant amounts of the contaminating proteins. HisHIV183 was extracted from the washed inclusion body pellet in the presence of 5M GuHCl. The 5M GuHCl extract was applied to a SEPHACRYL S-300 column and the appropriate fractions were pooled based on SDS-PAGE analysis. The amino acid sequence of the first ten residues was verified.

Refolding was performed at very low concentrations of protein, in the presence of DTT, lauryl maltoside and glycerol at 4° C. The diluted protein was concentrated on a Pro-RPC reversed phase column. Two peaks were obtained based on the UV and protein profile. Only Peak 1 has yielded soluble protein after stepwise dialysis. Far UV CD spectral analysis was used to monitor refolding from a denatured state at acid pH to a folded state at neutral pH. At pH 7.4, the protein was found to exhibit significant amounts of secondary structure that is consistent with that of beta sheet protein. At low pH, the CD spectrum showed that it is fully random coil, having a minimal molar ellipticity at 200 nm. The ratio of this minimum at 200 nm to that of the shoulder at 220 nm is approximately 4:1. This ratio decreased when the secondary structure formation occurred at neutral pH.

A UV scan at each step of dialysis showed that the protein recovery was >90% up to pH 7.4 and that there was no light scattering effect due to protein aggregates. SDS-PAGE analysis also indicated that there was no loss of protein up to pH 7.0 during refolding. Precipitation of protein occurred at the last step of dialysis, and the soluble protein was clarified by centrifugation. The overall protein recovery was about 0.10%. The refolded protein was found to be active in a trans-cleavage assay using the in vitro-translated 5A/5B substrate in the presence of 4A peptide.

We claim:

1. A method for determining whether a substrate is cleaved by a proteolytic enzyme, comprising:

(a) providing a proteolytic enzyme substrate that is modified at the amino-terminal or carboxy-terminal residue by synthetic attachment of a binding moiety;

(b) treating the modified substrate of step (a) with a proteolytic enzyme under conditions in which proteolysis can occur;

(c) coupling a ligand to a sensor chip, which ligand is capable of reversibly binding to the binding moiety of step (a);

(d) contacting the substrate of step (b) with the ligand of step (c) under conditions in which the ligand can reversibly bind to the binding moiety and form a complex; and (e) measuring the mass of the complex by surface plasmon technology, whereby measurement of a substantially lower mass for the treated substrate, compared to that of an untreated similarly complexed substrate, indicates cleavage by the enzyme.

2. The method of claim 1 wherein the substrate and the enzyme are from cytomegalovirus.

3. The method of claim 1 wherein the substrate and the enzyme are from hepatitis C virus.

4. The method of claim 1 wherein the binding moiety is phosphotyrosine and the ligand is an anti-phosphotyrosine monoclonal antibody.

5. The method of claim 1 wherein the substrate is further modified by synthetic attachment of a mass-increasing moiety at the end of the substrate opposite the end to which the binding moiety has been synthetically attached.

6. The method of claim 5 wherein the mass-increasing moiety is a polypeptide or a protein.

7. The method of claim 6 wherein the protein is streptavidin that is indirectly attached to the substrate through a bound biotin, which biotin is covalently linked to the substrate.

8. A method for identifying a proteolytic enzyme inhibitor in a sample, comprising:

(a) providing a proteolytic enzyme substrate that is modified at the amino terminal or carboxy terminal residue by synthetic attachment of a binding moiety;

(b) treating the modified substrate of step (a) with a proteolytic enzyme under conditions in which proteolysis can occur, both in the presence and absence of a sample suspected to contain an inhibitor of the proteolytic enzyme;

(c) coupling a ligand to a sensor chip, which ligand is capable of reversibly binding to the binding moiety of step (a);

(d) contacting the substrate of step (b) with the ligand of step (c) under conditions in which the ligand can reversibly bind to the binding moiety of step (a) and form a complex; and (e) measuring the mass of the complex by surface plasmon technology, whereby the presence of an inhibitor of the enzyme in the sample is indicated by measurement of a substantially higher mass, compared to that measured in the absence of the sample.

9. The method of claim 8 wherein the substrate and the enzyme are from cytomegalovirus.

10. The method of claim 8 wherein the substrate and the enzyme are from hepatitis C virus.

11. The method of claim 8 wherein the binding moiety is phosphotyrosine and the ligand is a phosphotyrosine monoclonal antibody.

12. The method of claim 8 wherein the substrate is further modified by synthetic attachment of a mass-increasing moiety at the end of the substrate opposite the end to which the binding moiety has been synthetically attached.

13. The method of claim 12 wherein the mass-increasing moiety is a polypeptide or a protein.

14. The method of claim 13 wherein the protein is streptavidin, that is indirectly attached to the substrate through a bound biotin, which biotin is covalently linked to the substrate.

* * * * *